United States Patent
Fayad et al.

(10) Patent No.: US 10,245,277 B2
(45) Date of Patent: *Apr. 2, 2019

(54) COMPOSITIONS, METHODS OF TREATMENT AND DIAGNOSTICS FOR TREATMENT OF HEPATIC STEATOSIS ALONE OR IN COMBINATION WITH A HEPATITIS C VIRUS INFECTION

(71) Applicant: VOLANT HOLDINGS GMBH, Feusisberg (CH)

(72) Inventors: Joseph M. Fayad, Las Vegas, NV (US); Jerome Schentag, Amherst, NY (US)

(73) Assignees: VOLANT HOLDINGS GMBH (CH); THERABRAKE, INC., Eggertsville, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/624,275

(22) Filed: Jun. 15, 2017

(65) Prior Publication Data
US 2018/0125870 A1 May 10, 2018

Related U.S. Application Data

(63) Continuation of application No. 15/162,941, filed on May 24, 2016, now Pat. No. 9,730,951, which is a continuation of application No. 14/002,642, filed as application No. PCT/US2012/026561 on Feb. 24, 2012, now Pat. No. 9,370,528, which is a continuation-in-part of application No. 12/932,633, filed on Mar. 2, 2011, now Pat. No. 9,757,346.

(60) Provisional application No. 61/551,638, filed on Oct. 26, 2011, provisional application No. 61/514,174, filed on Aug. 2, 2011, provisional application No. (Continued)

(51) Int. Cl.
| | |
|---|---|
| A61K 38/00 | (2006.01) |
| A61K 31/00 | (2006.01) |
| A61K 31/7004 | (2006.01) |
| A61K 45/06 | (2006.01) |
| A61K 38/21 | (2006.01) |
| A61K 31/7056 | (2006.01) |
| A61K 9/28 | (2006.01) |
| A61K 31/70 | (2006.01) |
| A61K 31/7072 | (2006.01) |
| A61K 35/741 | (2015.01) |
| A61K 9/20 | (2006.01) |
| A61K 31/555 | (2006.01) |
| A61K 36/05 | (2006.01) |
| A61K 36/48 | (2006.01) |
| A61K 36/8998 | (2006.01) |

(52) U.S. Cl.
CPC ........ *A61K 31/7004* (2013.01); *A61K 9/2009* (2013.01); *A61K 9/2013* (2013.01); *A61K 9/2054* (2013.01); *A61K 9/2059* (2013.01); *A61K 9/282* (2013.01); *A61K 9/2846* (2013.01); *A61K 31/00* (2013.01); *A61K 31/555* (2013.01); *A61K 31/70* (2013.01); *A61K 31/7056* (2013.01); *A61K 31/7072* (2013.01); *A61K 35/741* (2013.01); *A61K 36/05* (2013.01); *A61K 36/48* (2013.01); *A61K 36/8998* (2013.01); *A61K 38/21* (2013.01); *A61K 38/212* (2013.01); *A61K 45/06* (2013.01)

(58) Field of Classification Search
CPC ...... A61K 31/70; A61K 9/282; A61K 9/2846; A61K 31/00; A61K 31/7056; A61K 31/7072; A61K 31/35; A61K 31/741; A61K 38/21; A61K 38/212; A61K 45/06
USPC ...... 514/23, 43, 51, 474, 490; 424/451, 474, 424/490
See application file for complete search history.

(56) References Cited

U.S. PATENT DOCUMENTS

| | | | |
|---|---|---|---|
| 4,544,550 A | 10/1985 | Rodolfo | |
| 5,194,464 A | 3/1993 | Itoh et al. | |

(Continued)

FOREIGN PATENT DOCUMENTS

| | | |
|---|---|---|
| CN | 1194831 A | 10/1998 |
| CN | 1451388 A | 10/2003 |

(Continued)

OTHER PUBLICATIONS

Clark JM. et al. Roux-en-Y gastric bypass improves liver histology in patients in a mouse model of NASH. PLoS Obes. Res. 2005; 13(7): 1180-6.

(Continued)

*Primary Examiner* — Raymond J Henley, III
(74) *Attorney, Agent, or Firm* — J.A. Lindeman & Co., PLLC

(57) ABSTRACT

The present invention is directed to pharmaceutical compositions and methods of treatment that relate to the inhibition, resolution and/or prevention of an array of the manifestations of metabolic syndromes, including Type 2 diabetes, hyperlipidemia, weight gain, obesity, insulin resistance, hypertension, atherosclerosis, fatty liver diseases and certain chronic inflammatory states that lead to these manifestations, among others. In additional aspects, the present invention relates to compositions and methods which may be used to treat, inhibit or reduce the likelihood of hepatitis viral infections, including Hepatitis B and Hepatitis C viral infections, as well as the secondary disease states and/or conditions which are often associated with such viral infections, including hepatic steatosis (steatohepatitis), cirrhosis, fatty liver and hepatocellular cancer, among other disease states or conditions.

18 Claims, 10 Drawing Sheets

Related U.S. Application Data

61/480,788, filed on Apr. 29, 2011, provisional application No. 61/309,991, filed on Mar. 3, 2010.

(56) References Cited

U.S. PATENT DOCUMENTS

| | | | |
|---|---|---|---|
| 5,322,697 | A | 6/1994 | Meyer |
| 5,753,253 | A | 5/1998 | Meyer |
| 5,769,793 | A | 6/1998 | Pincus et al. |
| 6,248,363 | B1 | 6/2001 | Patel et al. |
| 6,267,988 | B1 | 7/2001 | Meyer |
| 6,270,774 | B1 | 8/2001 | Hsia et al. |
| 7,329,419 | B2 | 2/2008 | Yatcilla et al. |
| 8,367,418 | B2 | 2/2013 | Monte et al. |
| 8,394,845 | B2 | 3/2013 | Kim et al. |
| 9,370,528 | B2 * | 6/2016 | Schentag ............... A61K 45/06 |
| 9,730,951 | B2 * | 8/2017 | Fayad ................... A61K 45/06 |
| 9,757,346 | B2 * | 9/2017 | Fayad .................. A61K 31/195 |
| 2004/0028729 | A1 | 2/2004 | Shojaei et al. |
| 2006/0093592 | A1 | 5/2006 | Cheruvanky et al. |
| 2007/0014756 | A1 | 1/2007 | Touchet |
| 2007/0087957 | A1 | 4/2007 | Kidron |
| 2007/0172525 | A1 | 7/2007 | Sesha |
| 2008/0064632 | A1 | 3/2008 | Amatruda et al. |
| 2010/0130472 | A1 | 5/2010 | Young et al. |
| 2010/0152295 | A1 | 6/2010 | Karpf et al. |
| 2011/0046053 | A1 | 2/2011 | Kidron |
| 2011/0268795 | A1 | 11/2011 | Fayad et al. |
| 2013/0273154 | A1 | 10/2013 | Fayad et al. |
| 2013/0337055 | A1 | 12/2013 | Schentag et al. |
| 2014/0037739 | A1 | 2/2014 | Schentag et al. |
| 2015/0352189 | A1 | 12/2015 | Schentag et al. |
| 2017/0007631 | A1 | 1/2017 | Fayad et al. |
| 2017/0014436 | A1 | 1/2017 | Fayad et al. |

FOREIGN PATENT DOCUMENTS

| | | | |
|---|---|---|---|
| JP | 2007001945 | A | 1/2007 |
| RU | 2410108 | C1 | 1/2011 |
| WO | 2007022518 | A2 | 2/2007 |
| WO | 2010/027498 | A2 | 3/2010 |
| WO | 2010102041 | A2 | 9/2010 |
| WO | 2010027498 | A2 | 3/2011 |
| WO | 2012118712 | A2 | 7/2012 |
| WO | 2013148258 | A1 | 10/2013 |
| WO | 2014110090 | A1 | 7/2014 |

OTHER PUBLICATIONS

Minicis S. et al. HCC development is associated to peripheral insulin resistance in a mouse model of NASH. PLoS One, 2014; 9(5):e97136.

Di Bisceglie AM. et al. Serum alpha-fetoprotein levels in patients with advanced hepatitis C: results from the HALT-C Trial. J. Hepatol. 2005; 43(3):434-41.

Fayad J. et al. Stimulation of the ileal break hormones by an orally delivered natural product Aphoeline I to the terminal ileum in health volunteers. American Gastroenterology Association, 2010.

Van Wijk et al. C-reactive protein, fatal and nonfatal coronary artery disease, stroke, and peripheral artery disease in the prospective EPIC-Norfolk cohort study. Arterioscler Thromb. Vasc. Biol. 2013; 33(12):2888-94.

Furuya CK et al. Effects of bariatric surgery on nonalcoholic fatty liver disease: preliminary findings after 2 years. J. Gastroenterol. Hepatol. 2007; 22(4):510-4.

Glass LM et al. Total Body Weight Loss of >/=10% Is Associated with Improved Hepatic Fibrosis in Patients with Nonalcoholic Steatohepatitis. Dig. Dis. Sci. 2014.

Goff DC Jr. et al. 2013 ACC/AHA Guideline on the Assessment of Cardiovascular Risk: A Report of the American College of Cardiology/American Heart Association Task Force on Practice Guidelines. Circulation, 2013.

Jeong HC et al. Effect of stalin treatment in patients with acute myocardial infarction and left ventricular systolic dysfunction according to the level of high-sensitivity C-reactive protein. Int. Heart. J. 2014;55(2):106-12.

Jolly SS et al. Randomized Trial of Primary PCI with or without Routine Manual Thrombectomy. N. Engl. J. Med. 2015.

Liu X et al. Resolution on nonalcoholic steatohepatitis after gastric bypass surgery. Obes. Surg. 2007; 17(4):486-92.

Loombra R, Sanyal AJ. The global NAFLD epidemic. Nat. Rev. Gastroenterol. Hepatol. 2013;10(11):686-90.

Mathurin P. et al. Prospective study of the long-term effects of bariatric surgery on liver injury in patients without advanced diesease. Gastroenterology, 2009; 137)2):532-40.

Mattar SG et al. Surgically-induced weight loss significantly improves nonalcoholic fatty liver disease and the metabolic syndrome. Ann. Surg. 2005; 242(4):610-7; discussion 8-20.

National Cholesterol Education Program Expert Panel on Detection E, Treatment of High Blood Cholesterol in A. Third Report of the National Cholesterol Education Program (NCEP) Expert Panel on Detection, Evaluation, and Treatment of High Blood Cholesterol in Adults (Adult Treatment Panel III) final report, Circulation, 2002; 106(25):3143-421.

Patel NS et al. Effect of weight loss on magnetic resonance imaging estimation of liver fat and volume in patients with nonalcoholic steatohepatitis. Clin. Gastroenterol. Hepatol. 2015; 13(3):561-8 e1.

Pencina MJ et al. Application of New Cholesterol Guidelines to a Population-Based Sample. N. Engl. J. Med. 2014.

Steen DL, Bhatt DL Statin potency associated with incident diabetes in a real-world evaluation. Evid. Based Med. 2014;19(2):68.

Schwimmer JB et al. Magnetic resonance imaging and liver histology as biomarkers of hepatic steatosis in children with nonalcoholic fatty liver disease. Hepatology, 2014.

Siddique A. Kowdley KV Insulin resistance and other metabolic risk factors in the pathogenesis of hepatocellular carcinoma. Clin. Liver Dis. 2011; 15(2):281-96, vii-x.

Singh D et al. Imaging of non alcoholic fatty liver disease: A road less travelled. Indian J. Endocrinol. Metab. 2013;17(6): 990-5.

Sjostrom L et al. Lifestyle, diabetes, and cardiovascular risk factors 10 years after bariatric surgery. N. Engl. J. Med. 2004:351(26)2683-93.

Sjostrom L et al. Effects of bariatric surgery on mortality in Swedish obese subjects. N. Engl. J. Met 2007; 357(8): 741-52.

El-Serag Hepatocellular Carcinoma. The New England Journal of Medicine, 2011; 365(12):1118-1127.

Ochner CN et al. Changes in neurohormonal gut peptides following bariatric surgery. International Journal of Obesity, 2011; 35:153-166.

Hvidberg A et al. Effect of Glucagon-like Peptide 1 (proglucagon 78-107 amide) on Hepatic Glucose Production on Healthy Man. Metabolism, 1994; 43(1):104-108.

Reed MA et al. Roux-en-Y Gastric Bypass Corrects Hyperinsulinemia Implications for the Remission of Type 2 Diabetes. J. Clin. Endocrinol. Metab. 2011; 96:2525-2531.

Bikman BT et al. Mechanism for improved Insulin Sensitivity after Gastric Bypass Surgery. Endocrinol. Metab. 2008; 93:4656-4663.

Morinigo R et al. GLP-1 and Changes in Glucose Tolerance following Gastric Bypass Surgery in Morbidly Obese Subjects. Obesity Surgery, 2006; 16:1594-1601.

Morinigo R et al. Intra-abdominal Fat Adiponectin Receptors Expression and Cardiovascular Metabolic Risk Factors in Obesity and Diabetes. Obesity Surgery, 2006; 16:745-751.

Morinigo R et al. Glucagon-Like Peptide-1, Peptide YY, Hunger, and Satiety after Gastric Bypass Surgery in Morbidly Obese Subjects. The Journal of Clinical Endocrinology & Metabolism, 2006; 91(5):1735-1740.

Plum L et al. Comparison of Glucostatic Parameters After Hypocaloric Diet or Bariatric Surgery and Equivalent Height Loss. Obesity, 2011; 19:2149-2157.

Olbers T et al. Body composition, Dietary Intake, and Energy Expenditure After Laparoscopic Roux-en-Y Gastric Bypass and Laparoscopic Vertical Banded Gastroplasty. Ann. Surg. 2006; 244:715-722.

(56) References Cited

OTHER PUBLICATIONS

Ramon JM et al. Quality of food intake after bariatric surgery: vertical gastrectomy versus gastric bypass. Cir. Esp. 2012; 90(2):95-101.
Overs SE et al. Food Tolerance and Gastrointestinal Quality of Life Following Three Bariatric Procedures: Adjustable Gastric Banding, Roux-en-Y Gastric Bypass, and Sleeve Gastrectomy. Obes. Surg. 2012;22:536-543.
Shin AC, Berthoud HR. Food reward functions as affected by obesity and bariatric surgey. International Journal of Obesity, 2011; 35:S40-S44.
Leahy TM et al. Effects of bariatric surgery on food cravings: do food cravings and the consumption of craved foods "normalize" after surgery? Surgery for Obesity and Related Diseases, 2012; 8:84-91.
Brunault P et al. Observations Regarding 'Quality of Life' and 'Comfort with Food' After Bariatric Surgery: Comparison Between Laparoscopic Adjustable Gastric Banding and Sleeve Gastrectomy. Obes. Surg. 2011;21:1225-1231.
Shriner RL Food as a Bariatric Drug. Current Pharmaceutical Design, 2011;17:1198-1208.
Schweiger C et al. Effect of Different Bariatric Operations on Good Tolerance and Quality of Eating. Obes. Surg. 2010; 20:1393-1399.
Suter MD et al. A New Questionnaire for Quick Assessment of Food Tolerance after Bariatric Surgery. Obes. Surg. 2007:17:2-8.
Thomas JR, Marcus E. High and Low Fat Food Selection with Reported Frequency Intolerance Following Roux-en-Y Gastric Bypass. Obes. Surg. 2008; 18:282-287.
Miras AD, Roux CW. Bariatric surgery and tates: novel mechanisms of weight loss. Current opinion in Gastroenterology, 2010; 26:140-145.
Tulipani S et al. Metabolomics Unveils Urinary Changes in Subjects with Metabolic Syndrome following 12-Week Nul Consumption. J. Proteome Res. 2011; 10:5047-5058.
Ma J et al. A randomised trial of enteric-coated nutrient pellets to stimulate gastrointestinal peptide release and lower glycaemia in type 2 diabetes. Diabetologia, 2013; 56(6):1236-1242.
Cani et al. Improvement of Glucose Tolernace and Hepatic Insulin Sensitivity by Oligofructose Requires a Functional Glucagon-Like Peptide 1 Receptor. Diabetes, 2005;55:1484.
Cefalu. Medical Management of Diabetes Mellitus, 2000. CRC Press pp. 169 and 304.
Cherng J, Shih M. Improving Glycogenesis in Streptozocin (STZ) Diabetic Mice After Administration of Green Algae Chlorella. Life Sci. 2006; 78:1181.
Dumoulin et al. Peptide YY, Glucagon-Like Peptide-1, and Neurotensin Responses to Luminal Factors in the Isolated Vascularly Perfused Rat Ileum. Endocrinology, 1998; 139(9):3780-3786.
Egan J et al. GLP-1 Receptor Agonists are Growth and Differentiation Factors for Pancreatic Islet Beta Cells. Diabetes Metab. Res. Rev., 2003; 19:115.
Gross. Best practice in therapeutic drug monitoring. Br. J. Clin. Pharmacol., 1998; 46:95-99.
Grundy S et al. Definition of Metabolic Syndrome. Circulation, 2004; 109-433.
Hensrud D. Dietary Treatment and Long-Term Weight Loss and Maintenance in Type 2 Diabetes. Obesity Res. 2001;9:348S.
Holst. Therapy of type 2 diabetes mellitus based on the actions of glucagon-like peptide-1. Diabetes/Metabolism Res. Rev., 2002; 18:430-441.
Qbal et al. Mechanisms of Illeal Adaptation for Glucose Absorption after Proximal-Based Small Bowel Resection. J. Gastrointest. Surg. 2008; 12(11):1854-1865.
Kahn S et al. Mechanisms Linking Obesity to Insulin Resistance and Type 2 Diabetes. Nature, 2005, 444:840.
Kahn et al. Obesity and insulin resistance. The Journal of Clinical Investigation, 2000; 106(4):473-481.
Kelly DE. Sugars and starch in the nutritional management of diabetes mellitus. Am. J. Clin. Nutr. 2003;78 (suppl):858S-864S.
Knudson L. Glucagon-like Peptide-1: The Basis of a New Class of Treatment for Type 2 Diabetes. J. Med. Chem., 2004; 47:4128.
Li Z et al. Meta-Analysis: Pharmacologic Treatment of Obesity. Ann. Intern. Med., 2005; 142-532.
Magee HE, Reid E. The Absorption of Glucose from the Alimentary Canal. J. Physiol., 1931, 73:163.
Morton G et al. Leptin Action in the Forebrain Regulates the Hindbrain Response to Satiety Signals. Clin. Invest. 2005, 115:703.
Perley M, Kipnis D. Plasma Insulin Responses to Oral and Intravenous Glucose: Studies in Normal and Diabetic Subjects. Clin. Invest. 1967, 46:1954.
Ross R et al. Reduction in Obesity and Related Comorbid Conditions after Diet-Induced Weight Loss or Exercise-Induced Weight Loss in Men. Ann. Intern. Med., 2000, 133:92.
Sahra B et al. Targeting cancer cell metabolism: the combination of metformin and 2-deoxyglucose induced p53? dependent apoptosis in prostate cancer calls. Cancer Res., 2010, 70(6):abstract.
Strader AD et al. Weight Loss Through Ileal Transposition is Accompanied by Increased Ileal Hormone Secretion and Synthesis in Rats. J. Physiol. Endocrinol. Metab., 2004, 288:E447.
Vrang N et al. PPY (3-36) Reduces Food Intake and Body Weight and Improves Insulin Sensitivity in Rodent Models of Diet-induced Obesity. Am. J. Physiol. Regul. Integr. Comp. Physiol., 2006, 291:R367.
Zhao et al. Attenuation of insulin secretion by insulin-like growth factor 1 is mediated through activation of phosphodiesterase 3B. Proc. Natl. Acad. Sol., USA, 1997, 94:3223-3228.
Hosney et al., "Oral delivery of insulin from enteric-coated capsules containing sodium salicylate: effect on relative hypoglycemia of diabetic beagle dogs", International Journal of Pharmaceutics, 237, 2002, pp. 71-76.
Insulin (online) retrieved on Sep. 6, 2018 from https://medlineplus.gov/druginfo/meds/a682611.html; Sep. 5, 2018; 8 pages (year 2018).
Lim et a., "Insuin regulates glucagon-like Peptide-1 Secretion from the Enteroendocrine L Cell", Endocrinology, 2009, 150: 580-591.
Tsai et al., "Stimulation of leptin secretion by insulin", Indian J. Endocrinol. Metab., 2012, 16(suppl 3):S543-S548.
Marcellini P. Hepatitis C: the clinical spectrum of the disease. Journal of Hepatology, 1993, 31:9-16.
Butt AA, Kanwal F Boceprevir and Telaprevir in the Management of Hepatitis C Virus-Infected Patients. Reviews of Anti-Infective Agents, 2012, 54:96-104.
Armstrong MJ. Presence and severity of non-alcoholic fatty liver disease in a large prospective primary care cohort. Journal of Heptaology, 2012, 56:234-240.
Dowman JK et al. Current therapeutic strategies in non-alcoholic fatty liver disease. Diabetes, Obesity, and Metabolism, 2011, 13:692-702.
Lok AS et al. Evolution of Hepatic Steatosis in Patients with Advanced Hepatitis C: Results from the Hepatitis C Antiviral Long-Term Treatment Against Cirrhosis (HALT-C) Trial. Hepatology, 2009, 49:1828-1837.
Briceno J. et al. Impact of Donor Graft Steatosis on Overall Outcome and Viral Recurrence After Liver Transplantation for Hepatitis C Virus Cirrhosis. Liver Transplantation, 2009, 15:37-48.
Testino G. et al. Influence of Body Mass Index, Cholesterol, Triglycerides and Steatosis on Pegylated Interferon Alfa-2a and Ribovirin Treatment for Recurrent Hepatitis C in Patients Transplanted for HCV and Alcoholic Cirrhosis. hleptato-Gastroenterology, 2009, 56:501-503.
Pekow JR et al. Influence of Body Mass Index, Cholesterol, Triglycerides and Steatosis is Associated With Increased of Hepatocellular Carcinoma in Patients with Hepatitis C-Related Cirrhosis. American Cancer Society, 2007, 109:2490-2496.
Ghany MG et al. Predicting Clinical Outcomes Using Baseline and Follow-Up Laboratory Data from the Hepatitis C Long-Term Treatment Against Cirrhosis Trial. Hepatology, 2011, 54:1527-1537.
Thompson AJ et al. Viral clearance is associated with improved insulin resistance in genotype 1 chronic hepatitis C but not genotype 2/3. Gut, 2012, 61:128-134.

(56) References Cited

OTHER PUBLICATIONS

Lee WY et al. The effect of body mass index and fasting glucose on the relationship between blood pressure and incident diabetes mellitus: a 5-year follow-up study. Hypertension Research, 2011, 34:1093-1097.
Sung KC, Kim SH. Interrelationship between Fatty Liver and Insulin Resistance in the Development of Type 2 Diabetes. J. Clin. Endocrinol. Metab. 2011, 96(4):1093-1097.
Dixon JB et al. Nonalcoholic Fatty Liver Disease: Improvement in Liver Histological Analysis With Weight Loss. Hepatology, 2004, 39:1647-1654.
Hickman IJ et al. Should patients with type 2 diabetes and raised liver enzymes be referred for further evaluation of liver disease? Diabetes Research and Clinical Practice, 2008, 80:e10-e12.
Forlani G et al. Prevalence of elevated liver enzymes in Type 2 diabetes mellitus and its association with the metabolic syndrome. J. Endocrinol. Invest. 2008, 31:146-152.
Kirpich IA et al. Probiotics restore bowel flora and improve liver enzymes in human alcohol-induced liver injury: a pilot study. Alcohol, 2008, 42:675-682.
Fontana RJ et al. Serum Fibrosis Marker Levels Decrease After Successful Antiviral Treatment in Chronic Hepatitis C Patients with Advanced Fibrosis. Clinical Gastroenterology and Hepatology, 2009, 7:219-226.
Kwo PY et al. Efficacy of boceprevir, an NS3 protease inhibitor, in combination with peginterferon alfa-2b and ribavirin in treatment-naive patients with genotype 1 hepatitis C infection (SPRINT-1): an open-label, randomised, multicentre phase 2 trial. Lancet, 2010, 376:705-716.
Sherman KE et al. Response-Guided Telaprevir Combination Treatment for Hepatitis C Virus Infection. The New England Journal of Medicine, 2011, 365(11):1014-1024.
Bacon BR et al. Boceprevir for Previously Treated Chronic HCV Genotype 1 Infection. The New England Journal of Medicine, 2011, 364:(13):1207-1217.
Poordad F et al. Boceprevir for Untreated Chronic HCV Genotype 1 Infection. Journal of Medicine, 2011, 364: (13)1195-1206.
Poordad F et al. Medical resource utilisation and healthcare costs in patients with chronic hepatitis C viral infection and thrombocytopenia. Journal of Medical Economics, 2011, 14(2)194-206.
Poordad F. Big Changes Are Coming in Hepatitis C. Curr. Gastroenterol. Rep. 2011, 13:72-77.
Jacobson IM et al. Telaprevir for Previously Untreated Chronic Hepatitis C Virus Infection. The New England Journal of Medicine, 2011, 364(25):2405-2416.
Shah SR et al. Steatosis is an Independent Predictor of Relapse Following Rapid Virologic Response in Patients with HCV Genotype 3. Clinical Gastroenterology and Hepatology, 2011, 9:688-693.
Monte SV et al. Reduction in endotoxemia, oxidative and inflammtatory stress, and insulin resistance after Roux-en-Y gastric bypass surgery in patients with morbid obesity and type 2 diabetes mellitus. Surgery, 2012, 151:587-593.
Tamura Y et al. Serum Alpha-Fetoprotein Levels During and After Interferon Therapy and the Development of Hepatocellular Carcinoma in Patients with Chronic Hepatitis C. Dig. Dis. Sci. 2009, 54:2530-2537.
Chen CH et al. Clinical Significance of Elevated Alpha-Fetoprotein (AFP) in Chronic 1427 Hepatitis C without Hepatocelluylar Carcinoma. Hepato. Gastroenterology, 2008, 55:1423-.
Goldsteins NS et al. Serum alpha-Fetoprotein Levels in patients with Chronic Hepatitis C. Relationships with Serum Alanine Aminotransferase Values, Histologic Activity Index, and Hepatoxyte MIB-1 Scores. American Journal of Clinical Pathology, 1999, 111(6): 811-816.
Richardson P. et al. Determinants of Serum Alpha-Fetoprotein Levels in Hepatitis C Infected Patients. Clinical Gastroenterology and Hepatology, 2012, 10:428-433.
Oaski Y. et al. Decrease in alpha-fetoprotein levels predicts incidence of hepatocellular carcinoma in patients with hepatitis C virus infection receiving interferon therapy: a single center study. J. Gastroenterol. 2012, 47:444-451.
Tai WC et al. Clinical Implications of Alpha-fetoprotein in Chronic Hepatitiis C. J. Formos. Med. Assoc. 2009, 108 (3):210-218.
Chen TM et al. Predictors of alpha-fetoprotein elevation in patients with chronic hepatitis C, but not hepatocellular aarcinoma, and its normalization after pegylated interferon alfa 2a-riboviron combination therapy. Journal of Gastroenterology and Hepatology, 2007, 22:669-675.
Bisceglie AMD et al. Serum alpha-fetoprotein levels in patients with advanced hepatitis C: Results from HALT-O Trial. Journal of Hepatology, 2005, 43:434-441.
Holst JJ. Glucagonlike Peptide 1: A Newly Discovered Gastrointestinal Hormone. Gastroenterology, 1994, 107:1848-1855.
Ranganath IR et al. Attenuated GLP-1 secretion in obesity: cause or consequence? Gut, 1996, 38(6):916-919.
Pironi L et al. Fat-induced ileal brake in humans: a dose-dependent phenomenon correlated to the plasma levels of peptide YY. Gastroenterology, 1993, 105(3):733-739.
Monte SV et al. Characterization of Cardiovascular Outcomes in a Type 2 Diabetes Glucose Supply and Insulin Demand Model. Journal of Diabetes Science and Technology, 2010, 4(2):382-390.
Monte SV et al. Glucose Study and Insulin Demand Dynamics of Antidiabetic Agents. Journal of Diabetes Science and Technology, 2010, 4(2):365-381.
Guidone C et al. Mechanisms of Recovery From Type 2 Diabetes After Malabsorptive Bariatric Surgery. Diabetes, 2006, 55:2025-2031.
Welsh J et al. Insights from a Large Observational Database of Continuous Glucose Monitoring Adoption, Insulin Pump Usage and Glycemic Control: The CareLink Database. Pediatric Endocrinology Reviews, 2010, 7(3):413-416.
Welsh JA et al. Caloric Sweetener Consumption and Dyslipidemia Among US Adults. JAMA, 2010, 303 (15):1490-1497.
Baynes KCR et al. Regulation of food intake by gastrointestinal hormones. Curr. Opin. Gastroenterol. 2006, 22:626-631.
Burcelin R et al. Glucose Competence of the Hepatoportal Vein Sensor Requires the Presence of an Activated Glucagon-Like Peptide-1 Receptor Diabetes, 2001, 50:1720-1728.
Drucker DJ. Development of Glucagon-Like Peptide-1-Based Pharmaceuticals as Therapeutic Agents for the Treatment of Diabetes. Current Pharmaceutical Design, 2001, 7:1339-1412.
Drucker DJ. Glucagon-Like Peptide 2. The Journal of Clinical Endocrinology & Metabolism, 2001, 86(4):1759-1764.
Boushey RP et al. Glucagon-like Peptide (GLP)-2 Reduces Chemotherapy-associated Mortality and Enhances Cell Survival in Cells Expressing a Transfected GLP-2 Receptor. Cancer Research, 2001, 61:687-693.
Drucker DJ. Minireview: The Glucagon-Like Peptides. Endocrinology, 2001, 142(2):521-527.
Sumithran P. et al. Long-Term Persistence of Hormonal Adaptations to Weight Loss. The New England Journal of Medicine, 2011, 265:1597-1604.
Maljaars HPF et al. Ileal brake: A sensible food target for appetite control. A review. Physiology & Behavior, 2008, 95:271-281.

* cited by examiner

VISION, TASTE AND SMELL

NERVOUS CENTER EFFERENT AND AFFERENT SIGNALS TO THE GI TRACT

COMPOSITIONS, METHODS OF TREATMENT AND DIAGNOSTICS FOR TREATMENT OF HEPATIC STEATOSIS ALONE OR IN COMBINATION WITH A HEPATITIS C VIRUS INFECTION

RELATED APPLICATIONS

This application claims the benefit of priority of: U.S. patent application Ser. No. 15/162,941, filed May 24, 2016, which issued on Aug. 15, 2017 as U.S. Pat. No. 9,730,951, and is entitled "Compositions, Methods of Treatment and Diagnostics for Treatment of Hepatic Steatosis Alone or in Combination with a Hepatitis C Virus Infection"; which is a continuation of U.S. patent application Ser. No. 14/002,642, filed Aug. 30, 2013, which issued on Jun. 21, 2016 as U.S. Pat. No. 9,370,528, and is entitled "Compositions, Methods of Treatment and Diagnostics for Treatment of Hepatic Steatosis Alone or in Combination with a Hepatitis C Virus Infection"; which is a National Stage entry of PCT application serial number PCT/US12/26561, filed Feb. 24, 2012, entitled "Compositions, Methods of Treatment and Diagnostics for Treatment of Hepatic Steatosis Alone or in Combination with a Hepatitis C Virus Infection"; which is a continuation in part of U.S. patent application Ser. No. 12/932,633 filed Mar. 2, 2011, which issued as U.S. Pat. No. 9,757,346, and is entitled "Compositions and Methods for Inducing Satiety and Treating Non-Insulin Dependent Diabetes Mellitus, Prediabetic Symptoms, Insulin Resistance and Related Disease States and Conditions"; U.S. provisional patent applications Ser. No. 61/480,788, filed Apr. 29, 2011, and entitled, "Long Term Stimulation of Ileal hormones by an Orally Delivered, Ileal Released Natural Product Aphoeline"; U.S. provisional patent application Ser. No. U.S. 61/514,174, filed Aug. 2, 2011, and entitled, "Gut CFO: the ileal hormones. Decreasing insulin resistance, triglycerides, liver enzymes, signaling caloric intake, using caloric reserve, and turning body to health with every meal"; and U.S. provisional patent application Ser. No. U.S. 61/551, 638, filed Oct. 26, 2011, and entitled "Oral Formulations Mimetic of Roux-en-Y Gastric Bypass Actions on the Ileal Brake; Compositions, Methods of Treatment, Diagnostics and Systems for Treatment of Metabolic Syndrome Manifestations, Including Insulin Resistance, Fatty Liver Disease, Hyperlipidemia and Type 2 Diabetes", each of said applications being incorporated by reference in their entirety herein.

FIELD OF THE INVENTION

The present invention is directed to pharmaceutical compositions, methods of treatment, and diagnostics and computer-implementable systems that relate to the treatment of an array of the manifestations of metabolic syndromes, including Type 2 diabetes, hyperlipidemia, weight gain, obesity, insulin resistance, hypertension, atherosclerosis, fatty liver diseases and certain chronic inflammatory states that lead to these manifestations, among others. In additional aspects, the present invention relates to compositions and methods which may be used to treat, inhibit or reduce the likelihood of hepatitis viral infections, including Hepatitis B and Hepatitis C viral infections, as well as the secondary disease states and/or conditions which are often associated with such viral infections, including hepatic steatosis (steatohepatitis), cirrhosis, fatty liver and hepatocellular cancer, among other disease states or conditions.

BACKGROUND OF THE INVENTION

Hepatitis C infects 2-3% of the world's population, over 180 million persons, and is a cause of chronic hepatitis, liver cirrhosis, and hepatocellular carcinoma(1). The current standard of care, pegylated interferon plus ribavirin (pegIFN/Riba) combination therapy, is both expensive and poorly tolerated. Treatment efficacy is approximately 50%. Telaprevir and boceprevir, two direct acting antiviral (DAA) protease inhibitors, have recently been approved for clinical use in the US (2). Addition of either of these new agents has the potential to improve sustained virological response in hepatitis C to 65-75%. However, the addition of a DAA to the current standard of care introduces the risk of side effects, including anemia and rash, and failure to achieve Sustained viral response may pose an increased risk of accumulation protease inhibitor-resistant viral strains that may carry over resistance problems to future treatments. None of these current or future treatments appear to provide any benefit to the patient beyond suppression of the virus. Specifically, the liver is not healed even when viral counts are very low, the damage either ceases at the point of suppression, or inflammation and fibrosis may even progress slowly in the presence of a small number of residual viral particles. Hepatic steatosis, the primary accompanying condition of most patients with hepatitis C, continues and may progress even with complete viral suppression, and it is now time to propose that hepatic steatosis must be managed in lock step with the specific anti-viral treatments.

Hepatic steatosis is a common diagnosis in populations as a whole, often as frequent as 25% (3). There is no drug therapy for hepatic steatosis at the present time (4), most experts rely on lifestyle counseling alone. Of great concern, hepatic steatosis is a histologic feature in approximately two thirds of liver biopsies of patients with chronic hepatitis C. Until recently, this common finding was not carefully documented, and there were no large longitudinal studies describing the progression of steatosis in chronic hepatitis C or even hepatitis B. In 2009, Lok and colleagues examined changes in steatosis on serial biopsies among chronic hepatitis C patients participating in the Hepatitis C Antiviral Long-term Treatment against Cirrhosis (HALT-C) trial(5). All 1050 patients in this trial had advanced fibrosis at baseline biopsy and were documented not to have had a sustained virological response to pegIFN/Riba. Most (94%) of these patients had genotype 1 infection. At least one protocol follow-up biopsy was read on 892 patients, and 699 had the last biopsy performed 3.5 years after randomization. Hepatic damage was well advanced at enrollment, as 39% had cirrhosis and 61% had bridging fibrosis; 18%, 41%, 31%, and 10% had steatosis scores of 0, 1, 2, and 3 or 4, respectively. The mean steatosis score decreased in the follow-up biopsies in both the pegIFN/Riba-treated patients and controls with no effect of treatment assignment (P=0.66). A decrease in steatosis score by > or =1 point was observed in 30% of patients and was associated with both progression to cirrhosis and continued presence of cirrhosis (P=0.02). Compared to patients without a decrease in steatosis, those with a decrease in steatosis had worse metabolic parameters at enrollment, and were more likely to have a decrease in alcohol intake, improvement in metabolic parameters, and worsening liver disease (cirrhosis, esophageal varices, and deterioration in liver function). Lok and colleagues (5) concluded that hepatic steatosis recedes during progression from advanced fibrosis to cirrhosis. However, there was no available means to produce a decline in hepatic steatosis in most patients, which then became the primary motivation to discover a means of treating hepatic steatosis as an integral part of treatment of hepatitis C patients.

In a further definitive examination of the role of hepatic steatosis on the course of hepatitis C therapy, Briceno and colleagues (2009) examined livers that were to be transplanted into patients with hepatitis C that had already destroyed the original liver (6). The aim of this study was to determine the influence of donor graft steatosis on overall outcome, viral recurrence, and fibrosis progression in orthotopic liver transplantation for hepatitis C virus cirrhosis. One hundred twenty patients who underwent OLT for HCV cirrhosis between 1995 and 2005 were included in the study. Donor steatosis was categorized as absent (0%-10%; n=40), mild (10%-30%; n=32), moderate (30%-60%; n=29), or severe (>60%; n=19). A Cox multivariate analysis for marginal donor variables and a Model for End-Stage Liver Disease index were performed. Fibrosis evolution was analyzed in liver biopsies (fibrosis <2 or > or =2) 3, 6, and 12 months post-OLT and in the late post-OLT period. Fifty-six grafts were lost (46%). The survival of the grafts was inversely proportional to donor liver steatosis: 82%, 72%, and 72% at 1, 2, and 3 years post-OLT in the absence of steatosis; 73%, 63%, and 58% with mild steatosis; 74%, 62%, and 43% with moderate steatosis; and 62%, 49%, and 42% with severe steatosis (P=0.012). HCV recurrence was earlier and more frequent in recipients with steatosis >30% (46% versus 32% at 3 months, P=0.017; 58% versus 43% at 6 months, P=0.020; 70% versus 56% at 12 months, P=0.058; and 95% versus 69% at 3 years post-OLT, P=0.0001). (6). Graft survival was lower in alcoholic liver disease recipients versus HCV recipients when steatosis was >30% at 3, 6, and 12 months post-OLT (P=0.042) but not when steatosis was <30% (P=0.53). A higher fibrosis score was obtained 3 months post-OLT (P=0.033), 6 months post-OLT (P=0.306), 12 months post-OLT (P=0.035), and in the late post-OLT period (P=0.009). The authors concluded that the degree of hepatic steatosis in the new liver greatly influences the recurrence of hepatitis C and its progression in the new liver. In fact, Steatosis affects the success of treatment the second time. Hepatitis C recurrence was more frequent and earlier in recipients of moderately and severely steatotic livers. Fibrosis evolution is more rapid and severe when graft steatosis is >30% (6). As pointed out by Lok as well, there is a need to manage the hepatic steatosis in order to optimize the outcome of antiviral therapy for hepatitis C.

Testino and colleagues (2009) examined the influence of improvement in metabolic syndrome (typically associated with steatosis) biomarkers on the response of patients with hepatitis C to pegIFN/Riba (7). They examined baseline biomarkers such as Body Mass Index (BMI), cholesterol, triglycerides (TGs) and hepatic percentage of steatosis in the response to therapy with pegIFN/Riba in patients with recurrent hepatitis C (genotype 1). In this study, 30 consecutive prospectively followed patients diagnosed with recurrent hepatitis C were considered candidates for antiviral therapy. The observed distribution of BMI, cholesterol, TGs and steatosis were confirmed to be normally distributed by the one-sample Kolmogorov-Smirnov Goodness of fit test procedure. Comparison of BMI, cholesterol, TGs and steatosis between non responders (NR), sustained virological responders (SVR) and sustained biochemical responders (SBR) groups were analyzed by ANOVA with a post hoc Bonferroni test and correlation between variables was tested by Pearson test. The multivariate analysis was performed to estimate the chance of response on basis of the above mentioned variables. In patients with abnormal results in at least two out of four steatosis associated variables the chance of no-response was 40 times higher than that of SBR and 96 times than that of SVR (7). On the basis of these epidemiological studies, they argued that diet and exercise therapy should improve BMI, liver histology and, therefore, the response to pegIFN/Riba (7). Indeed this study provides further justification for concomitant use of a treatment for hepatic steatosis in conjunction with a treatment for the hepatitis C virus itself.

There is also evidence that management of hepatic steatosis in patients with hepatitis C would be of value in the prevention of hepatocellular carcinoma (HCC). For example, Pekow and colleagues (2007) (8) retrospectively identified 94 consecutive patients with hepatitis C cirrhosis who underwent liver transplantation from 1992 to 2005 and had pathology available for review. Of these, 32 had evidence of HCC, and 62 had no HCC on explant histology. All explant specimens were then graded for steatosis by a single, blinded pathologist. Next, hepatic steatosis, age, sex, BMI, HCV RNA, HCV genotype, Model for End-Stage Liver Disease (MELD) score, chronic alcohol use, and diabetes were examined in univariate and multivariate analyses for association with HCC. In total, 69% of patients in the HCC group and 50% of patients in the control group had evidence of hepatic steatosis (1+) on histology. Odds ratios for the development of HCC for each grade of steatosis compared with grade 0 were as follows: grade 1 (1.61 [0.6-4.3]), grade 2 (3.68 [1.1-12.8]), and grade 3 or 4 (8.02 [0.6-108.3]) (P=0.03 for the trend). In univariate analyses, there was a significant association between increasing steatosis grade (P=0.03), older age (56 years vs. 49 years; P<0.02), higher ALT aspartate aminotransferase (122.5 U/L vs. 91.5 U/L; P=0.005), higher AST alanine aminotransferase (95.8 U/L vs. 57.2 U/L; P=0.002), higher alpha-fetoprotein (113.5 ng/mL vs. 17.8 ng/mL; P<0.001), lower median HCV RNA (239,000 IU/mL vs. 496,500 IU/mL; P=0.02), higher biologic MELD score (21.8 vs. 20.3; P=0.03), and risk of HCC. In multivariate analysis, age (P=0.02), alpha-fetoprotein (P=0.007), and hepatic steatosis (P=0.045) were significantly associated with HCC (8). These authors concluded that in patients with Hepatitis C-related cirrhosis, the presence of hepatic steatosis is independently associated with the development of hepatocellular carcinoma (8). Clearly if the steatosis could be reversed, there is plausible evidence that HCC might be prevented or at least there would be fewer cases that progress to this deadly complication of the combined problem of hepatitis C and hepatic steatosis.

BRIEF DESCRIPTION OF THE INVENTION

In one aspect, the pesent invention is directed to pharmaceutical compositions, methods for the treatment, and diagnostics and computer-implementable systems that relate to the treatment of an array of the manifestations of metabolic syndromes, including Type 2 diabetes, hyperlipidemia, weight gain, obesity, insulin resistance, hypertension, atherosclerosis, fatty liver diseases and certain chronic inflammatory states that lead to these manifestations.

In an additional aspect of the invention, compositions and methods of treatment (which may entail concomitant pharmacological and/or surgical intervention e.g. Roux-en-Y gastric bypass (RYGB)) activate the ileal brake, which acts in the gastrointestinal tract and the liver of a mammal to control metabolic syndrome manifestations and thereby reverse or ameliorate the cardiovascular damage (atherosclerosis, hypertension, lipid accumulation, and the like) resulting from progression of metabolic syndrome. These compositions and/or methods may be used alone or in combination with additional bioactive agents, especially including anti-viral agents such as anti-hepatitis viral agents, especially anti-HCV agents and/or anti-HBV agents to treat the virus which is causing hepatitis as well as any secondary disease states and/or conditions which are caused by the viral infection. The effect of the present invention is synergistic in the patient or subject treated.

A primary target organ for improvement, reconstitution, or rehabilitation is the liver. The invention provides compositions, methods of treatment, diagnostics, and related systems useful in stabilizing blood glucose and insulin levels, control of hyperlipidemia, control of inflammation in organs tissues and blood vessel walls.

The present invention is also directed to combination (co-administration) treatment for use in viral infections that cause inflammation in the liver and well as numerous secondary disease states and/or conditions of the liver, including but not limited to Hepatitis C, Hepatitis B, Herpes Simplex virus, as well as any virus that causes injury to the mammal by causing inflammation and fibrotic changes in the liver. The effect of the present invention is synergistic. One aspect of this combination treatment consists of providing ileal brake hormone releasing therapy in combination with an antiviral drug active against the virus itself. This may entail administering an ileal brake compound (ileal brake hormone releasing substance) or compositions in combination with a bioactive agent such as an antiviral and/or anticancer agent, or alternatively, providing a method which activates the ileal brake such as a surgical intervention e.g. Roux-en-Y gastric bypass (RYGB)) in combination with the bioactive agent. The combination treatment of the present invention resolves the hepatic steatosis and thereby inhibits or otherwise reduces the likelihood of progressive injury to the liver that results from the fibrosis and cirrhosis, preferably in a synergistic manner.

The present invention provides that effective anti-viral treatment, including a cure of the viral infection, requires a composition which inhibits or otherwise treats the hepatic steatosis that is present in nearly all of these patients. This anti hepatic steatosis treatment must be effectively combined with a treatment active against the virus to increase the chances of both eradicating the virus and healing the injured liver. Thus, the invention provides methods of treatment and pharmaceutical compositions that can be used to prevent, reduce the likelihood of, or delay the onset of, a progressive damage to the liver which leads to cirrhosis, including fibrosis and related disease states and conditions of the condition, including hepatic steatosis and cirrhosis. It is noted that hepatic steatosis may also progress to hepatocellular carcinoma in patients with concomitant hepatitis viral infection, including hepatitis B and C virus infection. The combination of the present pharmaceutical composition with the anti-viral medication can be used to prevent, reduce the likelihood of, or delay the onset of, hepatocellular carcinoma in patients with hepatitis B and hepatitis C.

In one particular aspect of the invention, a novel formulation of glucose in dosages of approximately 10 grams or less per day, has both short and long term beneficial effects on patients with elevated triglycerides, insulin resistance and elevated liver enzymes indicative of hepatic steatosis. Dietary glucose and other sugars increase the manufacture of triglycerides which are prominent among the causes of fatty liver, and hepatic steatosis is an accessory pathway for viral replication. Dietary lipids accumulate in the liver as well. It is a recent discovery that releasing these dietary substances at a distal location in the intestine by the unique intestinal site targeted-release properties of the present formulations, can ameliorate not only the hyperglycemic manifestations of Type 2 diabetes, but also to control the accumulation of fat in the liver. These ileal brake compositions according to the present invention, when administered to a patient in need thereof, are useful to lower the patient's insulin resistance, lower triglycerides, reduce body weight, reduce HBA1c, and lower chronic liver inflammation (reduce ALT and AST), all in the manner similar to effect of RYGB surgery.

By means of careful study of enabling biomarkers, it becomes clear the ileal brake composition provides physiological and pharmaceutical actions on the same anatomical location of the patient and affects the same biochemical pathways as RYGB surgery, the biological target of both being the L-cells of the ileum and distal intestine.

In alternative embodiments, the present invention relates to compositions and methods useful for selective modulation of appetite in a manner similar to that of RYGB surgery. For example, the present invention also relates to ileal brake compositions (i.e., ileal brake hormone releasing substances), more particularly, a preferred oral formulation of ileal brake hormone releasing substances which contain a combination of carbohydrates and lipids, which are particularly adapted to treating insulin resistance and fatty liver, and are synergistic with specific anti-viral medicaments active against hepatitis viruses, including Hepatitis B and Hepatitis C viruses, among others.

Accordingly, the present invention also relates to a novel formulation and methods of treatment of disease states, disorders and/or conditions, or manifestations of hepatic steatosis, which is also known as fatty liver disease, non-alcoholic steatohepatitis (NASH) or non-alcoholic fatty liver disease (NAFLD). It should be added that there is no currently accepted pharmaceutical treatment for hepatic steatosis available, while it is acknowledged that both RYGB and the Brake formulation encompass the widest array of beneficial treatment thus far discovered.

DETAILED DESCRIPTION OF THE INVENTION

Figure 1:
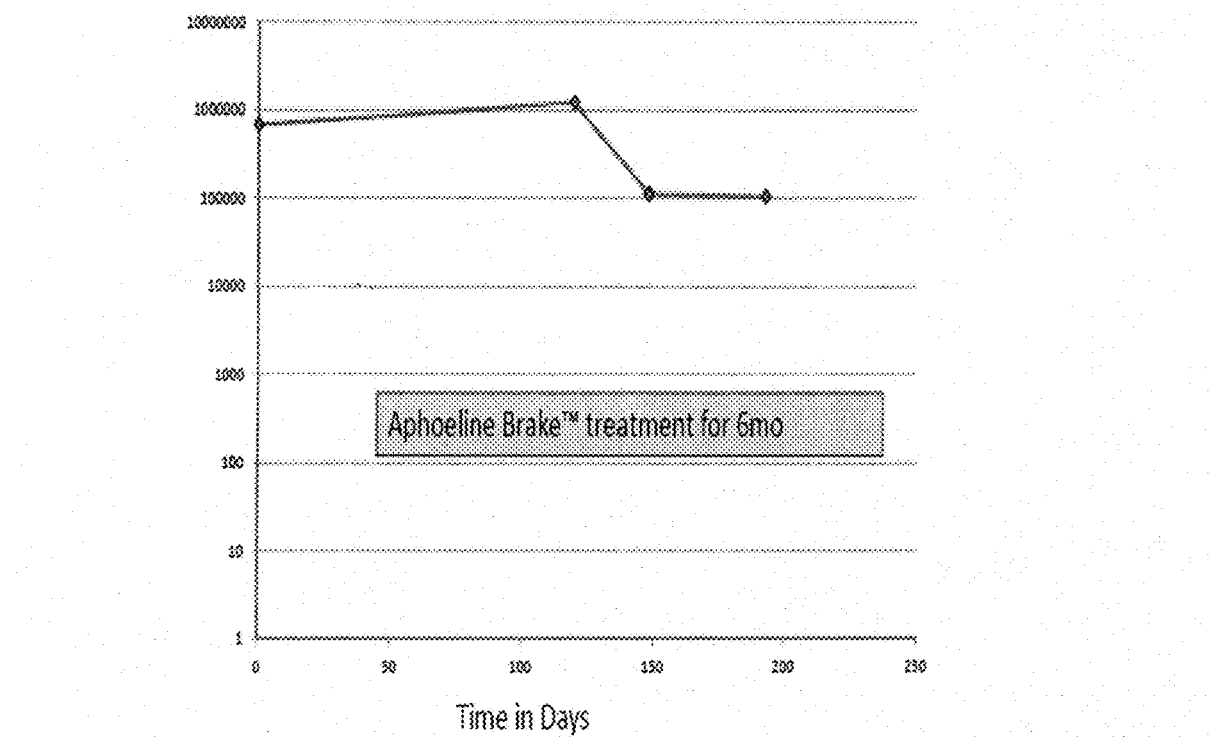
FIG. 1 shows that the hepatitis C viral count in a patient administered a composition according to the present invention decreased rapidly to 100K.

The following terms shall be used to describe the present invention. In instances where a term is not specifically defined herein, the term shall be accorded its meaning, within the context of its use, as understood by those of ordinary skill in the art.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The term "patient" or "subject" is used throughout the specification within context to describe an animal, generally a mammal, including a domesticated animal other than a laboratory animal (rat, mouse etc.) and preferably a human, to whom treatment, including prophylactic treatment (prophylaxis), with the compositions according to the present invention is provided. For treatment of those infections, conditions or disease states which are specific for a specific animal such as a human patient, the term patient refers to that specific animal.

The term "compound" shall mean any specific compound which is disclosed within this specification and typically means a single agent or a pharmaceutically acceptable salt thereof, or a bioactive agent or drug as otherwise described herein, including pharmaceutically acceptable salts thereof, generally a drug. Compounds are included in amounts effective to produce an intended physiological effect. Certain compounds according to the present invention may be used to treat secondary conditions such as type II diabetes, hepatic steatosis (steatohepatitis), cirrhosis, fatty liver and hepatocellular cancer or to suppress the immune system in liver transplant patients, or to treat viral infections directly (e.g., hepatitis B and/or C) in order to reduce the likelihood of a condition occurring or to advance therapies. Pharmaceutically acceptable salts are also compounds for use in the present invention.

The term "effective" when used in context, shall mean any amount of a compound or component which is used to produce an intended result within the context of its use. In the case of bioactive agents according to the present invention, the term effective generally refers to a therapeutically effective amount of compound which will produce an intended physiological effect associated with that agent, generally including antiviral activity. In the case of the treatment of hepatitis, hepatic steatosis (steatohepatitis), an effective amount of a compound or composition and/or bioactive agent is that amount which is effective to treat the condition which is being treated by administering the agent.

The term "hepatitis" is used to describe a liver condition which implies injury to the liver characterized by the presence of inflammatory cells in the tissue of the organ. The condition can be self-limiting, healing on its own, or can progress to scarring of the liver. Hepatitis is acute when it lasts less than six months and chronic when it persists longer than six months. A group of viruses known as the hepatitis viruses is principally responsible for most cases of liver damage worldwide. Hepatitis may run a subclinical course when the affected person may not feel ill. The patient becomes unwell and symptomatic when the disease impairs liver functions.

Hepatitis includes hepatitis from viral infections, including Hepatitis A through E (A, B, C, D and E-more than 95% of viral cause hepatitis, especially including hepatitis B and C), Herpes simplex, Cytomegalovirus, Epstein-Barr virus, yellow fever virus, adenoviruses; non-viral infections, including toxoplasma, Leptospira, Q fever and rocky mountain spotted fever, as well as alcohol, toxins, including amanita toxin in mushrooms, carbon tetrachloride, asafetida, among others, drugs, including paracetamol, amoxicillin, antituberculosis medicines, minocycline and numerous others as described herein.

The term "Hepatitis C Virus" or "HCV" is used to describe the various strains of Hepatitis C virus. HCV is one of several viruses that can cause hepatitis. It is unrelated to the other common hepatitis viruses (for example, hepatitis A or hepatitis B, among others). HCV is a member of the Flaviviridae family of viruses. Other members of this family of viruses include those that cause yellow fever and dengue. Viruses belonging to this family all have ribonucleic acid (RNA) as their genetic material. All hepatitis C viruses are made up of an outer coat (envelope) and contain enzymes and proteins that allow the virus to reproduce within the cells of the body, in particular, the cells of the liver. Although this basic structure is common to all hepatitis C viruses, there are at least six distinctly different strains of the virus which have different genetic profiles (genotypes). Treatment of HCV according to the present invention is directed to all strains of HCV, including the six or more distinct strains described above, as well as related strains which are drug resistant and multiple drug resistant strains. In the U. S., genotype 1 is the most common form of HCV. Even within a single genotype there may be some variations (genotype 1a and 1b, for example). Genotyping is viewed as important to guide treatment because some viral genotypes respond better to therapy than others. HCV genetic diversity is one reason that it has been difficult to develop an effective vaccine since the vaccine must protect against all genotypes.

A "Hepatitis C virus infection" or "Hepatitis C infection" is an infection of the liver caused by the hepatitis C virus (HCV).

The term "synergy" or "synergistic" refers to an effect or result on viral inhibition and/or hepatic steatosis, cirrhosis and/or hepatocellular cancer as evidenced by hepatic function (e.g., viral load in monitoring viral infection or a hepatic marker in monitoring hepatic steatosis) which is greater than that which is or would expected from a simple combination of therapies, or providing a more rapid return to normalcy, cure or cure rate. Thus, if one were to combine the administration of an ileal brake compound with that of an antiviral compound or compounds pursuant to the present invention, a synergistic result is that result which is greater than the additive result one would expect from combining the two therapies. A synergistic result for a particular compound or therapy is that result which occurs which is greater than the additive result or effect one would expect from simply doubling the dose of amount of a compound or composition used. By way of example (and not by limitation), for viral load reduction, additively will generally provide a 1 or 2 log reduction in viral titers, whereas synergy provides a 3 or 4 log reduction in viral titers. In the case of hepatic enzymes, additivity generally provides about 25% reduction for at least one liver enzyme (alanine amino transferase or ALT, aspartate amino transferase or AST, gamma-glutamyl transpeptidase or GGTP and alpha fetoprotein or AFP) and preferably at least two, at least three and preferably all four liver enzymes and synergy provides at least about 75-100% reduction in at least one liver enzymes (at least two, at three, at least four of the liver enzymes).

The term "hepatic steatosis" or "steatohepatitis" is used to describe a condition of the liver in which inflammation is caused by a buildup of fat in the liver. Hepatic steatosis is part of a group of liver diseases, known as nonalcoholic fatty liver disease ("fatty liver" or "fatty liver disease"), in which fat builds up in the liver and sometimes causes liver damage that gets worse over time (progressive liver damage). Nonalcoholic fatty liver disease (NAFLD) is fatty inflammation of the liver which is not due to excessive alcohol use, but is instead related to insulin resistance and metabolic syndrome, and responds to treatments according to the present invention which affects other insulin resistant states (e.g. diabetes mellitus type 2). Hepatic steatosis is the most extreme form of NAFLD, and is regarded as a major cause of cirrhosis of the liver. The present invention may be used to treat all forms of fatty liver disease, especially NAFLD, including hepatic steatosis.

Although a cause other than viral infection is not always known, hepatic steatosis seems also to be related to certain other conditions, including obesity, high cholesterol and triglycerides, and diabetes. Historically, treatment for hepatic steatosis involved controlling those underlying diseases. Ileal brake (ileal brake hormone releasing) compositions according to the present invention, either alone or in combination with antiviral agents and/or anticancer agents may be used to treat and/or reduce the likelihood of NASH, NAFLD and/or cirrhosis as well as liver cancer (hepatocellular carcinoma), especially when these disease states or conditions occur secondary to viral infection, especially a Hepatitis B or C viral infection.

Hepatic steatosis most commonly affects people who are middle-aged and are overweight or obese, have high cholesterol and triglycerides, or have diabetes. Despite these indications, hepatic steatosis can occur in people who have none of these risk factors. Excess body fat along with high cholesterol and high blood pressure are also signs of a condition called metabolic syndrome. This condition is closely linked to insulin resistance.

Along with excess fat in the liver, which many people have, several other factors, principally including viral infection, may contribute to the liver damage and place individuals at risk. These are:

Resistance to insulin, which means that the body can't use sugar (glucose) in the way it should. Normally, the body makes insulin after a meal is eaten that has sugar in it. Insulin helps the extra sugar in the blood get into muscles and liver. If the body does not respond to insulin in this way, then the sugar level in the blood will stay high. This is how insulin resistance can increase the chance of an individual developing type 2 diabetes.

Changes in how the liver makes fat and what the liver does with fat that is delivered to it by the intestines.

Other factors that have been known to contribute to hepatic steatosis include:

Surgeries that shorten the intestines, the stomach, or both, such as jejunal bypass operation or biliopancreatic diversion.

Use of a feeding tube or other method of receiving nutrition for a long time.

Use of certain medicines, including amiodarone, glucocorticoids, synthetic estrogens, and tamoxifen.

Hepatic steatosis usually gets worse over time (deemed "progressive"), especially where the patient is infected with a virus such as Hepatitis C or B. For this reason, a patient may have no symptoms until the disease progresses to the point that it begins to affect the way the liver works (liver function). As liver damage gets worse, symptoms such as tiredness, weight loss, and weakness may develop. It may take many years for hepatic steatosis to become severe enough to cause symptoms. In some limited cases, where viral infection is not implicated, the progress of the condition can stop and even reverse on its own without treatment. But in other cases, especially where viral infection is implicated, hepatic steatosis can slowly get worse and cause scarring (fibrosis) of the liver, which leads to cirrhosis and, in certain cases, hepatocellular carcinoma. In cirrhosis, the liver cells have been replaced by scar tissue. As more of the liver becomes scar tissue, the liver hardens and ceases to function normally.

The term "cirrhosis of the liver" or "cirrhosis" is used to describe a chronic liver disease characterized by replacement of liver tissue by fibrous scar tissue as well as regenerative nodules (lumps that occur as a result of a process in which damaged tissue is regenerated), leading to progressive loss of liver function. Cirrhosis is most commonly caused by fatty liver disease, especially including hepatic steatosis, as well as alcoholism and especially hepatitis B and C virus causing a low grade inflammation, which also causes hepatic steatosis, but has many other possible causes. Some cases are idiopathic, i.e., of unknown cause. Ascites (fluid retention in the abdominal cavity) is the most common complication of end stages of cirrhosis and is associated with a poor quality of life, increased risk of infection, and a poor long-term outcome. Other potentially life-threatening complications are hepatic encephalopathy (confusion and coma) and bleeding from esophageal varices. Prior to the present invention, hepatic steatosis and increasing hepatic cirrhosis was thought to be generally irreversible once it occurs, and historical treatment focused on preventing progression and complications. In advanced stages of cirrhosis, the only option is a liver transplant. The present invention may be used to limit, inhibit or reduce the likelihood or treat cirrhosis of the liver without regard to its etiology, although cirrhosis which is secondary to a viral hepatitis infection (especially including Hepatitis C and/or B) is a particular target of the present invention.

The term "treat", "treating", or "treatment", etc., as used herein, refer to any action providing a benefit to a patient for which the present compounds may be administered, including the treatment, inhibition or reduction in the likelihood (prevention) of metabolic syndromes, including Type 2 diabetes, hyperlipidemia, weight gain, obesity, insulin resistance, hypertension, atherosclerosis, fatty liver diseases and certain chronic inflammatory states that lead to these manifestations, among others. In additional aspects, the present invention relates to the treatment, inhibition or reduction in the likelihood (prevention) of hepatitis viral infections, including Hepatitis B and Hepatitis C viral infections, as well as the secondary disease states and/or conditions which are often associated with such viral infections, including hepatic steatosis (steatohepatitis), cirrhosis, fatty liver and hepatocellular cancer. Treatments with combination agents or combination therapy (e.g., ileal brake hormone releasing compound and antiviral agent and/or anticancer agents or antiviral agents and/or anticancer agents combined with Roux-en-Y gastric bypass surgery (RYGB)) represent preferred embodiments of the present invention.

The terms "ileal brake composition" and "ileal brake hormone releasing composition" are used in context to describe a compound or composition which comprises an "ileum hormone-stimulating amount of a nutritional substance" (also described as an "ileal brake hormone releasing substance" or "ileal brake compound" which includes any amount of a nutritional substance that is effective to induce measurable hormone release in the ileum, and induce feedback from the ileum or ileum-related stimulation of insulin secretion or inhibition of glucagon secretion, or other effect such as shutting down or decreasing insulin resistance and increasing glucose tolerance. The ileal brake composition used in the present invention may vary widely in dosage depending upon factors such as the specific nutrient at issue, the desired effect of administration, the desired goal of minimizing caloric intake, and the characteristics of the subject to whom the ileal brake hormone releasing substance is administered. Preferred ileal brake compounds/ileal brake hormone releasing substances which are included in ileal brake compositions according to the present invention include sugars, free fatty acids, lipids, polypeptides, amino acids, and compositions that yield sugars, free fatty acids, polypeptides, or amino acids upon digestion and mixtures thereof. In preferred aspects of the present invention the ileal brake compound/ileal brake hormone releasing substance is glucose, fructose, high fructose corn syrup and mixtures thereof and optionally, a GRAS lipid or triglyceride, selected from the group consisting of oil from nuts (various, such as peanut, cashew, walnut, pecan, brazil nuts, etc.), coconut, palm oil, corn oil, germ, olive oil, castor, sesame, fish oil (omega 3, oleic acid and derived liver oils) and mixtures thereof where the total amount of said ileal brake hormone releasing substance ranges from about 500 mg to about 12.5 grams, about 500 mg to about 7.5 grams, about 1 gram to about 5 grams about 500 mg to about 6 grams, 500 mg to about 3 grams, about 500 mg to about 2 grams. For example, in preferred aspects of the invention, at least about 500 mg of D-glucose is used, and a particularly preferred ileum hormonal-stimulating amount of D-glucose as the ileal brake compound includes between about 7.5-8 g to about 12-12.5 g (preferably around 10 g).

An ileal brake hormone releasing substance composition thus contains an effective amount of glucose or a related sugar (including but not limited to dextrose, sucrose, fructose) alone or in combination with oils (including but not limited to vegetable oils such as cottonseed, oils from most varieties of nuts, coconut, palm, corn, germ, olive, castor, sesame, fish oils including omega 3, oleic acid and derived liver oils). In the practice of the invention, oils, when included, are to be emulsified, allowed to become solids in emulsified form, and then coated for release in the ileum. When the ileal brake composition (Brake™) is produced to include both glucose and oil components as disclosed herein, the proportion of each of these components may vary from 10% by weight to 90% by weight. Indeed, it is envisioned by the inventors to produce a predominant glucose formulation, a predominant oil formulation and a 50:50 mixture of glucoses and oils and remain entirely within the spirit of the invention, since optimal formulations and combinations thereof can be defined by the direct impact on biomarkers of the ileal brake and biomarkers of hepatic steatosis.

In addition to the ileum hormone-stimulating amount of a nutritional substance (ileal brake compound) which is included in the ileal brake composition according to the present invention, the composition may also include "dietary components", which in addition to glucose, lipids and other components which are included herein (e.g., such as a micro-encapsulation of glucose, lipids and other nutritional components as described above) includes any natural substance which either itself evidences impact on the ileal brake, or alternatively, enhances the impact that glucose and/or lipids have on the ileal brake, such components including other complex carbohydrates and nutritional components as otherwise described herein including, for example, alfalfa leaf, chloretlla algae, chlorophyllin and barley juice concentrate, among a number of other agents, including probiotic bacteria, all of which are well known in the art.

Compositions for use in the present invention preferably comprise the micro-encapsulation of glucose, lipids and components of diet formulated to release these active compositions at pH values between about 6.8 and about 7.5, which allows substantial release and targets the action of said medicaments at the ileal brake in the distal intestine. Conventional formulation strategies used for pharmaceuticals never target release at pH values above 6.8, thereby releasing all of said pharmaceutical earlier in the intestine than the location of the L-cells and the ileal brake. The encapsulated compositions disclosed are a preferred medicament to reduce dietary glucose associated chronic inflammation, the primary driver of metabolic syndrome and eventual development of obesity and type 2 diabetes. Use of the encapsulated compositions according to the present invention decreases appetite for glucose, which is beneficial to the patient with metabolic syndrome, and thereby lowers both insulin resistance and inflammation and is of benefit to the treatment of patients with metabolic syndrome and related disease states or conditions including Type 2 diabetes, hyperlipidemia, weight gain, obesity, insulin resistance, hypertension, atherosclerosis, fatty liver diseases and certain chronic inflammatory states that lead to these manifestations, among others. In additional aspects, the above compositions may be used alone or co-administered with antiviral agents, including formulating with anti-viral agents to treat hepatitis viral infections, including Hepatitis B and Hepatitis C viral infections, as well as the secondary disease states and/or conditions which are often associated with such viral infections, including hepatic steatosis (steatohepatitis), cirrhosis, fatty liver and hepatocellular cancer, among other disease states or conditions.

Therapeutic methods according to the present invention may or may not include concomitant or even subsequent RYGB surgery, as control of metabolic syndrome and related conditions and/or disease states, as well as treating Hepatitis B and Hepatitis C viral infections, and the secondary disease states and/or conditions which are often associated with such viral infections, including hepatic steatosis (steatohepatitis), cirrhosis, fatty liver and hepatocellular cancer, among other disease states or conditions. In preferred practice of the invention, most treatment modalities would be possible with oral use of the disclosed ileal brake compositions, alone or in combination with an anti-viral gents(s), with the use of RYGB surgery reserved for cases beyond the control of said encapsulated compositions alone.

In a preferred embodiment of the invention, oral dosing with about 2,000 to about 10,000 milligrams, preferably about 3,000 to about 10,000 milligrams, about 7,500 to about 10,000 milligrams of a pharmaceutical formulation comprising microencapsulated glucoses, lipids, and/or amino acids activates the ileal brake in a dose increasing magnitude and treats one or more of the following components of metabolic syndrome: hyperlipidemia, weight gain, obesity, insulin resistance, hypertension, atherosclerosis, fatty liver diseases and chronic inflammatory states. In alternative embodiments, the ileal brake compositions as otherwise described herein are used to treat hepatitis viral infections, including Hepatitis B and Hepatitis C viral infections, as well as the secondary disease states and/or conditions which are often associated with such viral infections, including hepatic steatosis (steatohepatitis), cirrhosis, fatty liver and hepatocellular cancer, among other disease states or conditions.

In various embodiments according to the present invention, the disclosed formulations and compositions have been described as Aphoeline which is trademarked. The other trademarked name for the ileal brake hormone releasing substances is Brake. Compositions of the invention may be used alone or in combination with medicaments ordinarily used to treat specific manifestations of metabolic syndromes such as diabetes, hyperlipidemia, atherosclerosis, hypertension, obesity, insulin resistance, or chronic inflammation and/or anti-viral compounds which are used for the treatment of hepatitis B and/or hepatitis C infections. The benefit of combination is a broader spectrum action for treatment of metabolic syndrome than the single agent, and additional potency of the combination over its components. For example, compositions and methods of treatment of the invention may employ co-administration of a drug such as a biguanide antihyperglycemic agent (e.g. metformin); DPP-IV inhibitors (e.g. Vildagliptin, Sitagliptin, Dutogliptin, Linagliptin and Saxagliptin); TZDs or Thiazolidinediones (which are also known to be active on PPAR), e.g. pioglitazone, rosiglitazone, rivoglitazone, aleglitazar and the PPAR-sparing agents MSDC-0160, MSDC-0602; alpha glucosidase inhibitor including but not limited to acarbose (including delayed release preparations of Acarbose, Miglitol, and Voglibose); Glucokinase Activators including but not limited to TTP399 and the like; HMG-CoA reductase inhibitors. (examples of similar agents, thought to act on the defined statin pathway or by HMG-CoA reductase inhibition, include atorvastatin, simvastatin, lovastatin, ceruvastatin, pravastatin pitavastatin); angiotensin II inhibitors (AII inhibitors) (e.g. Valsartan, Olmesartan, Candesartan, Irbesartan, Losartan, Telmisartan and the like); a phosphodiesterase type 5 inhibitor (PDE5 inhibitor) such as sildenafil (Viagra), vardenafil (Levitra) and Tadalafil (Cialis®); Anti-obesity compositions that may benefit from combination with Brake™ include Lorcaserin and Topiramate; Combinations that will act beneficially on gastrointestinal flora include pH encapsulated pro-biotic organisms that release the live bacteria in the ileum at a pH of about 7.0 to 7.4, these pH encapsulated probiotic bacteria may be combined further with treatments for irritable bowel disease such as linaclotide or even with antibiotics where the goal is to restore bacterial flora after disruption by potent antibiotic therapy. Anti-viral agents including anti-hepatitis B agents and anti-hepatitis C agents are as otherwise described herein and include, for example, Hepsera (adefovir dipivoxil), lamivudine, entecavir, teibivudine, tenofovir, emtricitabine, clevudine, valtoricitabine, amdoxovir, pradefovir, racivir, BAM 205, nitazoxanide, 231-B, Bay 41-4109, EHT899, zadaxin (thyrnosin alpha-1) and mixtures thereof for hepatitis B infections and ribavirin, pegylated interferon, boceprevir, daclatasvir, asunaprevir, INX-189, FV-100, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, GS 9256, GS 9451, GS 5885, GS 6620, GS 9620, GS9669, ACH-1095, ACH-2928, GSK625433, TG4040 (MVA-HCV), A-831, F351, NS5A, NS4B, ANA598, A-689, GNI-104, IDX102, ADX184, ALS-2200, ALS-2158, BI 201335, BI 207127, BIT-225, BIT-8020, GL59728, GL60667, PSI-938, PSI-7977, PSI-7851, SCY-635, TLR9 Agonist, PHX1766, SP-30 and mixtures thereof for hepatitis C infections.

The term "anti-Hepatitis C agent" or "anti-HCV agent" is used throughout the specification to describe an agent which may be used in the treatment of HCV and/or secondary disease states and/or conditions of HCV infection and includes such agents as ribavirin, pegylated interferon, boceprevir, daclatasvir, asunaprevir, INX-189, FV-100, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, GS 9256, GS 9451, GS 5885, GS 6620, GS 9620, GS9669, ACH-1095, ACH-2928, GSK625433, TG4040 (MVA-HCV), A-831, F351, NS5A, NS4B, ANA598, A-689, GNI-104, IDX102, ADX184, ALS-2200, ALS-2158, BI 201335, BI 207127, BIT-225, BIT-8020, GL59728, GL60667, PSI-938, PSI-7977, PSI-7851, SCY-635, TLR9 Agonist, PHX1766, SP-30 and mixtures thereof, especially including one or more of the above in combination with ribavirin. Anti-HCV agents which may be used in the present invention may be formulated in pharmaceutical compositions which include an effective amount of an ileal brake composition, which is formulated for release in the ileum pursuant to the present invention and may include immediate release and/or sustained release and/or controlled release compositions and/or components of anti-HCV agents as otherwise described herein.

The term "anti-Hepatitis B agent" or "anti-HBV agent" is used throughout the specification to describe an agent which may be used in the treatment of HBV and includes such agents as Hepsera (adefovir dipivoxil), lamivudine, entecavir, telbivudine, tenofovir, emtricitabine, elevudine, valtoricitabine, amdoxovir, pradefovir, racivir, BAM 205, nitazoxanide, UT 231-B, Bay 41-4109, EHT899, zadaxin (thymosin alpha-1) and mixtures thereof. Anti-HBV agents which may be used in the present invention may be formulated in pharmaceutical compositions which include an effective amount of an ileal brake composition, which is formulated for release in the ileum pursuant to the present invention and may include immediate release and/or sustained release and/or controlled release compositions and/or components of anti-HBV agents as otherwise described herein.

The term "anticancer agent" or "antihepatocellular cancer agent" is used throughout the specification to describe an anticancer agent which may be used to inhibit, treat or reduce the likelihood of hepatocellular cancer, of the metastasis of that cancer. Anticancer agents which may find use in the present invention in combination with an ileal brake hormone releasing compound and in certain instances, such compounds which are further combined with an anti-HCV or anti-HBV agent, include for example, nexavar (sorafenib), sunitinib, bevacizumab, tarceva (erlotinib), tykerb (lapatinib) and mixtures thereof. In addition, other anticancer agents may also be used in the present invention, where such agents are found to inhibit metastasis of cancer, in particular, hepatocellular cancer.

Other aspects of the invention relate to compositions which comprise an effective amount of an ileal brake hormone releasing substance as otherwise described herein, preferably glucose or dextrose which is formulated in delayed and/or controlled release dosage form in order to release an effective amount of ileal brake hormone releasing substance in the ileum of the patient or subject to whom compositions according to the present invention are administered, generally, at least about 50% of the total amount of the ileal brake hormone releasing substance present, and preferably at least about 70%, at least about 75%, at least about 80%, at least about 85%, at least about 90%, and at least about 95% or more of the ileal brake hormone releasing substance present in the composition. In the case of D-glucose or dextrose as the ileal brake hormone releasing substance, it is preferred that at least about 2.5 grams, at least about 3 grams, at least about 7.5 grams and more preferably about 10-12.5 grams or more of glucose be released in the patient's or subject's ileum in order to stimulate ileal hormone release.

Compositions according to the present invention comprise effective amounts of ileal brake hormone releasing substance, preferably D-glucose or dextrose, which may be combined with at least one delayed or controlled release component such as a delayed/controlled release polymer or compound such as a cellulosic material, including, for example, ethyl cellulose, methyl cellulose, hydroxymethylcellulose, hydroxypropylcellulose, polyvinylpyrrolidone, cellulose acetate trimellitiate (CAT), hydroxypropylmethyl cellulose phthalate (HPMCP), polyvinyl acetate phthalate (PVAP), cellulose acetate phthalate (CAP), shellac, copolymers of methacrylic acid and ethyl acrylate, copolymers of methacrylic acid and ethyl acrylate to which a monomer of methylacrylate has been added during polymerization, a mixture of amylose-butan-1-ol complex (glassy amylose) with Ethocel® aqueous dispersion, a coating formulation comprising an inner coating of glassy amylose and an outer coating of cellulose or acrylic polymer material, pectins (of various types), including calcium pectinate, carageenins, aligns, chondroitin sulfate, dextran hydrogels, guar gum, including modified guar gum such as borax modified guar gum, beta-cyclodextrin, saccharide containing polymers, e.g., a polymeric construct comprising a synthetic oligosaccharide-containing biopolymer including methacrylic polymers covalently coupled to oligosaccharides such as cellobiose, lactulose, raffinose and stachyose, or saccharide-containing natural polymers including modified mucopolysaccharides such as cross-linked pectate; methacrylate-galactomannan, pH-sensitive hydrogels and resistant starches, e.g., glassy amylose. Other materials include methylmethacrylates or copolymers of methacrylic acid and methylmethacrylate having a pH dissolution profile that delays release in vivo of the majority of the ileal brake hormone releasing substance until the dosage form reaches the ileum may also be used. Such materials are available as Eudragit® polymers (Rohm Pharma, Darmstadt, Germany). For example, Eudragit® L100 and Eudragit® S100 can be used, either alone or in combination. Eudragit® L100 dissolves at pH 6 and upwards and comprises 48.3% methacrylic acid units per g dry substance; Eudragit® S100 dissolves at pH 7 and upwards and comprises 29.2% methacrylic acid units per g dry substance. Generally, the encapsulating polymer has a polymeric backbone and acid or other solubilizing functional groups. Polymers which have been found suitable for purposes of the present invention include polyacrylates, cyclic acrylate polymer, polyacrylic acids and polyacrylamides. A particularly preferred group of encapsulating polymers are the polyacrylic acids Eudragit® L and Eudragit® S which optionally may be combined with Eudragit® RL or RS. These modified acrylic acids are useful since they can be made soluble at a pH of 6 or 7.5, depending on the particular Eudragit chosen, and on the proportion of Eudragit® S to Eudragit® L, RS, and RL used in the formulation. By combining one or both of Eudragit® L and Eudragit® S with Eudragit® RL and RS (5-25%), it is possible to obtain a stronger capsule wall and still retain the capsule's pH-dependent solubility.

A delayed and/or controlled release oral dosage form used in the invention can comprise a core containing an ileum hormonal-stimulating amount of an ileal brake hormone releasing substance along with carriers, additives and excipients that is coated by an enteric coating. In some embodiments, the coating comprises Eudragit® L100 and shellac, or food glaze Eudragit® S100 in the range of 100 parts L100:0 parts S100 to 20 parts L100:80 parts S100, more preferably 70 parts L100:30 parts S100 to 80 parts L100:20 parts S100. In preferred alternatives, the preferred coating is a nutrateric coating which dissolves at the pH of the ileum (about 7-8, about 7.2-8.0, about 7.4-8.0, about 7.5-8.0) comprising a shellac, and emulsifiers such as triacetone and hypromellose, among others. Alternative nutrateric coatings include ethyl cellulose, ammonium hydroxide, medium chain triglycerides, oleic acid, and stearic acid. As the pH at which the coating begins to dissolve increases, the thickness necessary to achieve ileum-specific delivery decreases. For formulations where the ratio of Eudragit® L100:S100 is high, a coat thickness of the order 150-200 μm can be used. For coatings where the ratio Eudragit® L100:S100 is low, a coat thickness of the order 80-120 μm can be used in the present invention.

Compositions for use in the present invention preferably comprise the micro-encapsulation of the ileal hormone releasing compounds, e.g., glucose, lipids and dietary components as described hereinabove formulated to release these active compositions at pH values between about 6.8 and about 7.5 preferably about 7.0 to about 7.5, which allows substantial release and targets the action of said medicaments at the ileal brake in the distal intestine. Conventional formulation strategies used for pharmaceuticals never target release at pH values above 6.8. These compositions may be used alone or formulated in combination with an anti-viral agent (preferably an anti-HCV or anti-HBV agent) or other bioactive agent (an anticancer agent effective for example in the treatment of hepatocellular cancer) as otherwise described herein, where the antiviral and/or other bioactive agent is formulated as an immediate release composition and/or a sustained and/or controlled release composition in combination with the ileal hormone releasing compounds. Use of the encapsulated compositions according to the present invention decreases appetite for glucose, which is beneficial to the patient with metabolic syndrome, and thereby lowers both insulin resistance and inflammation and is of benefit to the treatment of patients with metabolic syndrome and related disease states or conditions including Type 2 diabetes, hyperlipidemia, weight gain, obesity, insulin resistance, hypertension, atherosclerosis, fatty liver diseases and certain chronic inflammatory states that lead to these manifestations, among others. In additional aspects, the above compositions may be used alone or co-administered with anti-viral agents, including formulating with anti-viral agents to treat hepatitis viral infections, including Hepatitis B and Hepatitis C viral infections, as well as the secondary disease states and/or conditions which are often associated with such viral infections, including hepatic steatosis (steatohepatitis), cirrhosis, fatty liver and hepatocellular cancer, among other disease states or conditions.

Compositions according to the present invention may be administered at various times during the day (e.g., once a day, twice a day, four times a day) in order to produce the intended effect, i.e., effective treatment of metabolic syndrome, including Type 2 diabetes, hyperlipidemia, weight gain, obesity, insulin resistance, hypertension, atherosclerosis, fatty liver diseases and certain chronic inflammatory states that lead to these manifestations, among others, as well as to treat, inhibit or reduce the likelihood of hepatitis viral infections, including Hepatitis B and Hepatitis C viral infections, as well as the secondary disease states and/or conditions which are often associated with such viral infections, including hepatic steatosis (steatohepatitis), cirrhosis, fatty liver and hepatocellular cancer, among other disease states or conditions related to same. Preferably, compositions according to the present invention are administered once daily, whereby all components, i.e., the ileal hormone release compound and any bioactive agent (including an antiviral agent and/or an anticancer agent as otherwise described herein), if included, are in sustained or controlled release form. In certain aspects, the ileal hormone release compound is in sustained or controlled release form and the bioactive agent is in both immediate and sustained or controlled release form.

In another embodiment, the invention provides a method of treatment comprising once-daily administration to the subject of a delayed and/or controlled release oral dosage form with the target site being the ileal brake. In this aspect of the invention, the dosage form is administered while the subject is in the fasted state and at a time of around six to around nine hours prior to the subject's next intended meal. The dosage form comprises an enterically-coated, ileum hormone-stimulating amount of ileal brake hormone releasing substance and releases the majority of the ileal brake hormone releasing substance in vivo upon reaching the subject's ileum. This formulation may be used alone or in combination with another bioactive agent, including an anti-viral agent such as an anti-HCV or anti-HBV agent or an anticancer agent. Additionally, this formulation may be further combined with immediate, sustained or controlled release bioactive agent, including an anti-viral agent such as an anti-HCV or anti-HBV agent or anticancer agent, or combined with both immediate and sustained or controlled release bioactive agent in order to influence the bioavailability of the bioactive agent combined with the ileal break hormone releasing substance.

In still another embodiment, the invention provides a method of treatment by administering to the subject a delayed and/or controlled release oral dosage form comprising an enterically-coated, ileum hormone-stimulating amount of an ileal brake hormone releasing substance. The dosage form is administered while the subject is in the fasted state and at a time of around four and one-half to ten hours, more preferably around six to around nine hours prior to the subject's next intended meal. The dosage form comprises an enterically-coated, ileum hormone-stimulating amount of ileal brake hormone releasing substance and releases the majority of the ileal brake hormone releasing substance in vivo upon reaching the subject's ileum. This formulation may be used alone or in combination with another bioactive agent, including an anti-viral agent such as an anti-HCV or anti-HBV agent. Additionally, this formulation may be further combined with immediate, sustained or controlled release bioactive agent, including an anti-viral agent such as an anti-HCV or anti-HBV agent, or combined with both immediate and sustained or controlled release bioactive agent in order to influence the bioavailability of the bioactive agent combined with the ileal break hormone releasing substance.

In still other preferred embodiments, the invention provides methods for control of metabolic syndrome and its various detrimental actions, through specific biochemical pathways that stabilize blood glucose and insulin levels, and treating gastrointestinal and hepatic inflammatory disorders comprising once-daily administration to a subject in need thereof of a delayed and/or controlled release composition which may comprise an emulsion or a microemulsion containing an ileum hormone-stimulating amount of ileal brake hormone releasing substance. The composition is administered while the subject is in the fasted state and at a time of around four to ten, preferably around six to around nine hours prior to the subject's next intended meal. The composition releases the majority of the ileal brake hormone releasing substance in vivo upon reaching the subject's ileum, the site of its intended effect. Other bioactive agents are released pursuant to the formulation provided, whether immediate release, sustained or controlled release or immediate and sustained or controlled release.

In preferred embodiments of the aforementioned methods of treatment of the invention, the dosage form is administered once-daily at bedtime, or in AM.

By administering the dosage form to a subject in the fasted state at around four to ten, around six to around nine hours prior to the subject's next intended meal, and delivering substantially all of the ileal brake hormone releasing substance to the ileum, methods and compositions of the invention achieve improved levels of plasma gastrointestinal hormones and prove useful in the treatment or prevention of one or more of metabolic syndrome and/or type II diabetes mellitus, as well as hyperlipidemia, weight gain, obesity, insulin resistance, hypertension, atherosclerosis, fatty liver diseases and certain chronic inflammatory states that lead to these manifestations, among others, as well as hepatitis viral infections, including Hepatitis B and Hepatitis C viral infections, as well as the secondary disease states and/or conditions which are often associated with such viral infections, including hepatic steatosis (steatohepatitis), cirrhosis, fatty liver and hepatocellular cancer, among other disease states or conditions The benefit of obtaining at least twenty-four hour appetite suppression and improved blood glucose and insulin levels from a single oral dosage of an inexpensive ileal brake hormone releasing substance alone or in combination with a bioactive agent as otherwise described herein increases the likelihood that the subject will adhere to the methods of treatment for an extended time (improved patient compliance), thereby achieving a maximum health benefit. Further, compositions and methods of the invention utilize ileal brake hormone releasing substances that are free of the safety and cost concerns associated with pharmacological and surgical intervention, and can induce long-term control of appetite, inflammation, insulin resistance and hyperlipidemia.

In another embodiment, the invention provides a delayed and/or controlled release oral dosage form comprising an effective amount of an ileal brake hormone releasing substance, preferably D-glucose or dextrose in an amount effective when released in the ileum to stimulate or inhibit the release of hormones in that portion of the small intestine of a subject or patient. This dosage form is administered in accordance with, and achieves the advantages of, the aforementioned methods of treatment of the invention. In addition, the present invention provides a method for diagnosing metabolic syndrome (glucose intolerance) and/or type II diabetes in a patient or subject.

Thus, the invention provides methods of stimulating or inhibiting the hormones (depending on the hormone) of the ileum in an easy and reproducible or standardized way (orally) which did not exist prior to the present method. Indeed, RYGB surgery is the only other way to release these ileal brake hormones and invoke mimicry of the effects of the present invention. Pursuant to the present application, the testing on a large scale of the ileal release to study and classify the variation or pathology of the hormone releases as such release relates to control of metabolic syndromes or type 2 diabetes and related pathological states and conditions, and the effect these hormones have on the rest of the metabolic and hormonal status of the body is another aspect of the invention. Thus, the present method allows the introduction of one or more dosages in oral dosage form to the ileum of the patient which can be standardized sufficiently to allow the creation of a normal reference range for the hormonal stimulation. It has been discovered that the present invention can be used to probe different diseases stemming from the relative or absolute increase or decrease of the ileal hormones, not only in treating the overweight/obesity metabolic syndrome axis but a number of other gastrointestinal diseases as otherwise described herein.

In particular aspects, the present invention is directed to treating, inhibiting or reducing the likelihood of hepatitis infections, especially including hepatitis C or B viral infections and secondary disease states and conditions which may occur as a consequence of such infection, which may include metabolic syndrome, Type 2 diabetes, hyperlipidemia, weight gain, obesity, insulin resistance, hypertension, atherosclerosis, fatty liver diseases and certain chronic inflammatory states that lead to these manifestations, and especially such secondary disease states and conditions including hepatic steatosis (steatohepatitis), cirrhosis, fatty liver and hepatocellular cancer, among other disease states or conditions.

Particular and preferred methods of the present invention include the following:

Hepatic Steatosis, fatty liver disease, NASH and NAFLD may be effectively treated by an orally administered, ileal brake hormone releasing substance according to the present invention which lowers elevated insulin resistance, and lowers elevated liver enzymes such as ALT and AST, and lowers serum triglycerides by mimicry of the effect of surgery, preferably Roux-en-Y gastric bypass surgery (RYGB).

The hepatic steatosis treatment as described above, may be preferably combined with an anti-viral drug active against Hepatitis C and/or Hepatitis B, to lower elevated virus counts and concomitantly improve the health of the steatotic cells in liver of the patient with hepatitis C.

In the hepatic steatosis treatment described above, the primary beneficial action of the ileal brake hormone releasing substance (ileal brake compound) is to decrease the supply of glucose to the liver and triglyceride synthesis that the virus also uses as part of this pathway to reproduce, and thereby lower the degree of fatty accumulation in the liver, and limit viral reproduction and further injury to the liver.

The synergistic combination of the specific antiviral treatment and ileal brake hormone releasing substance combination used for treatment of hepatitis C (and in certain instances, hepatitis B); where the primary beneficial action of the antiviral is to decrease the viral injury to steatotic hepatic cells and the primary beneficial action of the ileal brake hormone releasing substance (ileal brake compound) is to decrease the supply of glucose and triglycerides synthesis in the liver, and thereby lower the number of hepatic cells that become steatotic and at risk for extension of the viral infection and further hepatic injury. The favorable effect on other secondary conditions such as cirrhosis, fatty liver and hepatocellular cancer is also significant and in most instances, synergistic.

The present invention is also directed to the synergistic combination treatment for hepatitis C by administering an ileal brake compound as described above in combination with an anti-hepatitis C viral agent wherein the antiviral medicament is pegylated interferon and/or ribavirin in a therapeutically useful dosage and duration. This treatment can be used alone or combined with an effective amount of at least one additional anti-HCV agent as otherwise described herein. These agents include, for example, boceprevir, daclatasvir, asunapavir, INX-189, FV-100, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, GS 9256, GS 9451, GS 5885, GS 6620, GS 9620, GS9669, ACH-1095, ACH-2928, GSK625433, TG4040 (MVA-HCV), A-831, F351, NS5A, NS4B, ANA598, A-689, GNI-104, IDX102, ADX184, ALS-2200, ALS-2158, BI 201335, BI 207127, BIT-225, BIT-8020, GL59728, GL60667, PSI-938, PSI-7977, PSI-7851, SCY-635, TLR9 Agonist, PHX1766, SP-30 and mixtures thereof. These agents may be used alone, in combination, or further in combination with effective amounts of ribavirin, pegylated interferon or mixtures thereof.

For example, in a particular aspect, the present invention is directed to the synergistic co-administration of an ileal brake compound/composition with an effective antiviral combination of pegylated interferon and/or ribavirin in a therapeutically useful dosage and duration, combined with boceprevir in a dosage of at least 800 mg three times daily.

In a further aspect, the present invention is directed to the synergistic co-administration of an ileal brake compound/composition with an effective antiviral combination of pegylated interferon and/or ribavirin in a therapeutically useful dosage and duration, combined with telaprevir in a dosage of at least 750 mg three times daily.

In a further aspect, the present invention relates to a synergistic co-administration of an ileal brake compound/composition with an effective antiviral combination of the NS5A replication complex inhibitor daclatasvir in an effective dose combined with the NS3 protease inhibitor asunaprevir in an effective dose and either or both of these protease inhibitors can be used alone or in combination with pegylated interferon and/or ribavirin in an effective amount.

In still an additional aspect, the present invention relates to a synergistic co-administration of an ileal brake compound/composition with an effective antiviral in combination wherein the antiviral medicament is daclatasvir, an NS5A replication complex inhibitor used in an effective amount alone or in combination with pegylated interferon and/or ribavirin in an effective amount.

In still another aspect, the present invention relates to a synergistic co-administration of an ileal brake compound/composition with an effective antiviral in combination, wherein the antiviral medicament is asunaprevir a NS3 protease inhibitor used in an effective amount alone or in combination with pegylated interferon and/or ribavirin in an effective amount.

In yet an additional aspect, the present invention relates to a synergistic co-administration of an ileal brake compound/composition with an effective antiviral in combination, wherein the antiviral medicament is IN X-189 a nucleotide polymerase inhibitor used in an effective amount, alone or in combination with pegylated interferon and/or ribavirin in an effective amount.

In still another aspect, the present invention relates to a synergistic co-administration of an ileal brake compound/composition with an effective antiviral in combination, wherein the antiviral medicament is FV-100, a bicyclic nucleoside analogue, used in an effective amount, alone or in combination with pegylated interferon and/or ribavirin in an effective amount.

In still another aspect, the present invention relates to a synergistic co-administration of an ileal brake compound/composition with an effective antiviral in combination, wherein the antiviral medicament is GS 9190, a non-nucleoside polymerase inhibitor, used in an effective amount, alone or in combination with pegylated interferon and/or ribavirin in an effective amount.

In still another aspect, the present invention relates to a synergistic co-administration of an ileal brake compound/composition with an effective antiviral in combination, wherein the antiviral medicament is GS 9256, a NS3 protease inhibitor, used in an effective amount, alone or in combination with pegylated interferon and/or ribavirin in an effective amount.

An additional aspect of the present invention relates to a synergistic co-administration of an ileal brake compound/composition with an effective antiviral in combination, wherein the antiviral medicament is GS 9451, a NS3 protease inhibitor, used in an effective amount, alone or in combination with pegylated interferon and/or ribavirin in an effective amount.

In still a further aspect, the present invention relates to a synergistic co-administration of an ileal brake compound/composition with an effective antiviral in combination, wherein the antiviral medicament is GS 5885, a NS5A inhibitor, used in an effective amount, alone or in combination with pegylated interferon and/or ribavirin in an effective amount.

In another aspect, the present invention relates to a synergistic co-administration of an ileal brake compound/composition with an effective antiviral in combination, wherein the antiviral medicament is GS 6620, a nucleotide polymerase inhibitor, used in an effective amount, alone or in combination with pegylated interferon and/or ribavirin in an effective amount.

Still another aspect or the present invention relates to a synergistic co-administration of an ileal brake compound/composition with an effective antiviral in combination, wherein the antiviral medicament is GS 9620, a TLR-7 agonist, used in an effective amount, alone or in combination with pegylated interferon and/or ribavirin in an effective amount.

In another aspect, the present invention relates to a synergistic co-administration of an ileal brake compound/composition with an effective antiviral in combination, wherein the antiviral medicament is GS 9669, a non-nucleoside polymerase inhibitor, used in an effective amount, alone or in combination with pegylated interferon and/or ribavirin in an effective amount.

In a further aspect, the present invention relates to a synergistic co-administration of an ileal brake compound/composition with an effective antiviral in combination, wherein the antiviral medicament is PSI-938, a guanine nucleotide analog polymerase inhibitor, used in an effective amount, alone or in combination with pegylated interferon and/or ribavirin in an effective amount.

In yet another aspect, the present invention relates to a synergistic co-administration of an ileal brake compound/composition with an effective antiviral in combination, wherein the antiviral medicament is PSI-7977, a nucleotide analog, used in an effective amount, alone or in combination with pegylated interferon and/or ribavirin in an effective amount.

In yet a further aspect, the present invention relates to a synergistic co-administration of an ileal brake compound/composition with an effective antiviral in combination, wherein the antiviral medicament is SCY-635, a non-immunosuppressive cyclophilin inhibitor, used in an effective amount, alone or in combination with pegylated interferon and/or ribavirin in an effective amount.

In another aspect, the present invention relates to a synergistic co-administration of an ileal brake compound/composition with an effective antiviral in combination, wherein the antiviral medicament is BI 201335, an inhibitor of NS3/4A protease, used in an effective amount, alone or in combination with pegylated interferon and/or ribavirin in an effective amount.

In yet another additional aspect, the present invention relates to a synergistic co-administration of an ileal brake compound/composition with an effective antiviral in combination, wherein the antiviral medicament is BI 207127, an inhibitor of the NS5B non-nucleoside polymerase, used in an effective amount, alone or in combination with pegylated interferon and/or ribavirin in an effective amount.

In an additional aspect, the present invention relates to a synergistic co-administration of an ileal brake compound/composition with an effective antiviral in combination, wherein the antiviral medicament is ACH-2928, an inhibitor of the NS5A non-nucleoside polymerase, used in an effective amount, alone or in combination with pegylated interferon and/or ribavirin in an effective amount.

In another aspect, the present invention relates to a synergistic co-administration of an ileal brake compound/composition with an effective antiviral in combination, wherein the antiviral medicament is INX-189, a protide which is a phosporamidate nucleotide analog used in an effective amount, alone or in combination with pegylated interferon and/or ribavirin in an effective amount.

In another aspect, the present invention relates to a synergistic co-administration of an ileal brake compound/composition with an effective antiviral in combination, wherein the antiviral medicament is ALS-2200, an inhibitor of the NS5B non-nucleoside polymerase used in an effective amount alone or with pegylated interferon and/or ribavirin in an effective amount.

In an additional aspect, the present invention relates to a synergistic co-administration of an ileal brake compound/composition with an effective antiviral in combination, wherein the antiviral medicament is ALS-2158, an inhibitor of the NS5B non-nucleoside polymerase used in an effective amount alone or with pegylated interferon and/or ribavirin in an effective amount.

In yet a further aspect, the present invention relates to a synergistic co-administration of an ileal brake compound/composition with an effective antiviral in combination, wherein the antiviral medicament is BIT-225, an inhibitor of the targeted p& protein used in an effective amount, alone or with pegylated interferon and/or ribavirin in an effective amount.

In another further aspect, the present invention relates to a synergistic co-administration of an ileal brake compound/composition with an effective antiviral in combination, wherein the antiviral medicament is BL-8020, an inhibitor of Hepatitis C virus (HCV)-induced autophagy used in an effective amount alone or with pegylated interferon and/or ribavirin in an effective amount.

Predictive Methods for Response in Hepatitis C Patients

Predicting clinical outcomes in patients with chronic hepatitis C is considered challenging. Ghany and colleagues (9) used the Hepatitis C Long-Term treatment against Cirrhosis (HALT-C) trial database to develop two prediction models, using baseline values of routinely available laboratory tests together with changes in these values during follow-up to predict clinical decompensation and liver-related death/liver transplant in patients with advanced hepatitis C. Patients randomized to no treatment and who had >/=2-year follow-up without a clinical outcome were included in the analysis. Four variables (platelet count, aspartate aminotransferase [AST]/alanine aminotransferase [ALT] ratio, total bilirubin, and albumin) with three categories of change (stable, mild, or severe) over 2 years were analyzed. Cumulative incidence of clinical outcome was determined by Kaplan-Meier analysis and Cox regression was used to evaluate predictors of clinical outcome. In all, 470 patients with 60 events were used to develop models to predict clinical decompensation. Baseline values of all four variables were predictive of decompensation. There was a general trend of increasing outcomes with more marked worsening of laboratory values over 2 years, particularly for patients with abnormal baseline laboratory test values. A model that included baseline platelet count, AST/ALT ratio, bilirubin, and severe worsening of platelet count, bilirubin, and albumin was the best predictor of clinical decompensation. A total of 483 patients with 79 events were used to evaluate predictors of liver-related death or liver transplant. A model that included baseline platelet count and albumin as well as severe worsening of AST/ALT ratio and albumin was the best predictor of liver-related outcomes. These authors concluded that both the baseline value and the rapidity in change of the value of routine laboratory variables were shown to be important in predicting clinical outcomes in patients with advanced chronic hepatitis C (9).

Another means of predicting response of Hepatitis C to pegIFN/Riba is the viral response linked change in insulin resistance, a parameter of interest to us because it is one of the earliest effects of both RYGB and Brake™ In their study, Thompson and colleagues (10) examined genotype-specific associations between hepatitis C virus and insulin resistance. Specifically, this study investigated the association between a sustained virological response (SVR) and insulin resistance after chronic treatment with interferon/ribavirin therapy. They enrolled 2255 treatment-naive patients with chronic HCV genotype 1 or 2/3 from two phase 3 trials where patients were treated for either 24 or 48 weeks. Insulin resistance was measured before treatment and 12 weeks after treatment using homeostasis model assessment (HOMA)-IR. Paired HOMA-IR measurements were available in 1038 non-diabetic patients (497 with genotype 1; 541 with genotype 2/3). At baseline the prevalence of HOMA-IR>3 was greater in patients with genotype 1 than 2/3 (33% vs. 27%; p=0.048). There was a significant reduction in the prevalence of IR in patients with genotype 1 achieving SVR (delta 10%; p<0.001), but not in genotype 1 non-responders or those with genotype 2/3. Multivariate analysis indicated that SVR was associated with a significant reduction in mean HOMA-IR in patients with genotype 1 (p=0.004), but not in those with genotype 2/3, which was independent of body mass index, ALT, GGTP and lipid level changes. It was thought that genotype 1 may have a direct effect on the development of insulin resistance, independent of host metabolic factors, and may be partially reversed by viral eradication (10). This study partially justifies the study of parameters linked to hepatic steatosis, but this variable was not directly measured in this trial.

Several studies of T2D and metabolic syndrome patients with and without Hepatitis C provide further support for Hepatic steatosis, common in diabetes, (11, 12) as the usual cause of elevated liver enzymes, and link the insulin resistance, glucose intolerance and elevated triglycerides to the development of hepatic steatosis. Stated simply, the steatosis is present because of the metabolic syndrome even without overt T2D. Once present, the hepatic steatosis interacts with the hepatitis C virus to make eradication more difficult. Finally, the liver enzymes only decline in hepatitis C treatments where the metabolic syndrome is also resolved, such as in the study of Thompson (10). Dixon and colleagues (13) directly studied the effect of gastric banding associated weight loss on nonalcoholic fatty liver disease in a case series of 36 selected obese patients. These 36 patients (11 males, 25 females) had paired liver biopsies, the first at the time of laparoscopic adjustable gastric band placement and the second after weight loss. Second biopsies were obtained from two groups: those requiring a subsequent laparoscopic procedure (n=19) and those with index biopsy score of 2 or greater for zone 3-centric hepatic fibrosis (n=17). All biopsies were scored, blinded to the patient's identity and clinical condition, for individual histological features and for NASH stage and grade. Initial biopsies demonstrated NASH in 23 patients and steatosis in 12 patients. Repeat biopsies were taken at 25.6+/−10 months (range, 9-51 months) after band placement. Mean weight loss was 34.0+/−17 kg, and percentage of excess weight loss was 52+/−17%. There were major improvements in lobular steatosis, nacre-inflammatory changes, and fibrosis at the second biopsy (P<0.001 for all). Portal abnormalities remained unchanged. Only four of the repeat biopsies fulfilled the criteria for NASH, implying that this procedure was essentially a cure. There were 18 patients with an initial fibrosis score of 2 or more compared with 3 patients at follow-up (P0.001). The patients with the metabolic syndrome in this series (n=23) who had more extensive changes before surgery, had greater improvement with resulting weight loss. Dixon and colleagues concluded that weight loss after bariatric surgery provides major improvement or resolution of obesity and metabolic syndrome-associated abnormal liver histological features in severely obese subjects (13).

Hickman and colleagues noted that raised liver enzymes are common in type 2 diabetes (T2DM) but often considered benign. Non-alcoholic fatty liver, including hepatic steatosis was the cause in 65% of cases but other causes included alcoholic liver disease and viral hepatitis. Cirrhosis was identified in 11 patients. These investigators noted a significant burden of advanced liver diseases from a variety of etiologies in patients with T2DM. (14).

Forlani conducted an observational point prevalence study on hepatic disease and raised liver enzymes in Type 2 diabetes in eight hospital-based Italian diabetes units. Data of 9621 consecutive Type 2 diabetes patients (males, 52.4%; median age, 65 yr) were analyzed, and alanine and aspartate aminotransferase (ALT, AST) and gamma-glutamyl transferase (GGPT) levels were related to body mass index (BMI), metabolic control and the presence of the metabolic syndrome. They noted ALT, AST, and GGPT levels exceeding the upper limit of normal were present in 16.0%, 8.8%, and 23.1%, respectively, the prevalence being higher in males, increasing with obesity class and poor metabolic control, and decreasing with age. Elevated enzymes were systematically associated with most parameters of the metabolic syndrome. After correction for age, gender, BMI, and differences across centers, elevated triglyceride levels/fibrate treatment [odds ratio (OR), 1.57; 95% confidence interval (CI), 1.34-1.84] and an enlarged waist circumference (OR, 1.47; 95% CI, 1.17-1.85) were the only parameters independently associated with high ALT. In a separate analysis, the presence of metabolic syndrome (Adult Treatment Panel III criteria) was highly predictive of raised liver enzymes. After exclusion of hepatitis B and C positive cases, tested in 2 centers, the prevalence of raised enzymes decreased by approximately 4%, but the association with the metabolic syndrome did not change significantly. In conclusion, the high prevalence of elevated liver enzymes in Type 2 diabetes is in keeping with the well-demonstrated risk of progressive liver disease (15).

Probiotics are closely associated with metabolic syndrome and hepatic steatosis. A study by Kirpich and colleagues examined the potential therapeutic role of probiotics in alcohol-induced liver injury in 66 adult Russian males admitted to a psychiatric hospital with a diagnosis of alcoholic psychosis. Patients were randomized to receive 5 days of Bifidobacterium bifidum and *Lactobacillus plantarum* 8PA3 versus standard therapy alone (abstinence plus vitamins). Stool cultures and liver enzymes were performed at baseline and again after therapy. Results were compared between groups and with 24 healthy, matched controls who did not consume alcohol. Compared to healthy controls, alcoholic patients had significantly reduced numbers of bifidobacteria (6.3 vs. 7.5 log colony-forming unit [CFU]/g), lactobacilli (3.15 vs. 4.59 log CFU/g), and enterococci (4.43 vs. 5.5 log CFU/g). The mean baseline ALT, AST, and GGTP activities were significantly elevated in the alcoholic group compared to the healthy control group (AST: 104.1 vs. 29.15 U/L; ALT: 50.49 vs. 22.96 U/L; GGT 161.5 vs. 51.88 U/L), indicating that these patients did have mild alcohol-induced liver injury. After 5 days of probiotic therapy, alcoholic patients had significantly increased numbers of both bifidobacteria (7.9 vs. 6.81 log CFU/g) and lactobacilli (4.2 vs. 3.2 log CFU/g) compared to the standard therapy arm. Despite similar values at study initiation, patients treated with probiotics had significantly lower AST and ALT activity at the end of treatment than those treated with standard therapy alone (AST: 54.67 vs. 76.43 U/L; ALT 36.69 vs. 51.26 U/L). In a subgroup of 26 subjects with well-characterized mild alcoholic hepatitis (defined as AST and ALT greater than 30 U/L with AST-to-ALT ratio greater than one), probiotic therapy was associated with a significant end of treatment reduction in ALT, AST, GGT, lactate dehydrogenase, and total bilirubin. In this subgroup, there was a significant end of treatment mean ALT reduction in the probiotic arm versus the standard therapy arm. In conclusion, patients with alcohol-induced liver injury have altered bowel flora compared to healthy controls. Short-term oral supplementation with *B. bifidum* and *L. plantarum* 8PA3 was associated with restoration of the bowel flora and greater improvement in alcohol-induced liver injury than standard therapy alone(16). This study points to additional methods for control of hepatic inflammation and liver enzyme elevation.

Progressive liver disease in hepatitis C is also monitored with biomarkers of hepatic fibrosis. Fontana and colleagues examined serum fibrosis marker levels during the lead-in treatment phase of patients enrolled in the Hepatitis C Antiviral Long-term Treatment against Cirrhosis (HALT-C) trial. After the trial, the week 0, 24, 48, and 72 serum samples were analyzed for YKL-40, tissue inhibitor of matrix metalloproteinase-1, amino-terminal peptide of type III procollagen (PIIINP), and hyaluronic acid (HA) levels. All 456 chronic hepatitis C patients received pegIFN/Riba for 24 to 48 weeks. Mean age of the patients was 49.2 years, 71% were male, and 39% had cirrhosis at baseline. Lower pretreatment serum YKL-40, tissue inhibitor of matrix metalloproteinase-1, PIIINP, and HA levels were associated significantly with a week-20 early virologic response (P<0.0001). In multivariate analysis, non-1 genotype, non-black race, prior interferon monotherapy, and lower baseline serum ALT/AST levels and log (10)YKL-40 levels were associated independently with week-20 virologic response. Statistically significant declines in all marker levels were observed at week 72 compared with baseline in the 81 patients with a sustained virologic response, but not in the 72 patients with breakthrough or relapse. At weeks 24 and 48, significant increases were observed in serum PIIINP and HA levels in nonresponders compared with virologic responders (P<0.0001). Fontana and colleagues concluded that elevated pretreatment YKL-40 levels are an independent predictor of initial virologic response to pegIFN/Riba treatment. Levels of all 4 serum fibrosis markers decreased significantly in the SVR patients, consistent with reduced hepatic fibrogenesis. Measuring serum fibrosis marker levels before and after antiviral therapy may provide important indicators of response in patients with hepatitis C (17).

New agents are here for treatment of hepatitis C, for example boceprevir, an NS3 protease inhibitor, which is approved for use in combination with pegIFN/Riba. PegIFN/Riba alone achieves sustained virological response (SVR) in fewer than half of patients with genotype 1 chronic hepatitis C virus infection treated for 48 weeks. Kwo and colleagues tested the efficacy of boceprevir, an NS3 hepatitis C virus oral protease inhibitor, when added to pegIFN/Riba for genotype 1 hepatitis C virus. The primary endpoint was SVR 24 weeks after treatment. In patients with untreated genotype 1 chronic hepatitis C infection, the addition of the direct-acting antiviral agent boceprevir to standard treatment with pegIFN/Riba doubles the sustained response rate compared with that recorded with standard treatment alone (18). There are similar studies with telaprevir. Although over 60% of the study patients have hepatic steatosis at baseline, data on any endpoint of response other than viral load is completely absent in these studies, and there are no biomarkers of metabolic syndrome measured or assessed.

Thus, it does not appear that the newer drugs such as boceprevir or telaprevir change liver enzymes or any marker of hepatic steatosis in patients, even though these two newer protease inhibitor drugs are used in combination with pegIFN/Riba (2, 19-24).

Regarding the role of antiviral agents in the control of hepatic steatosis, it would be unexpected to see change in liver enzymes or resolution of hepatic inflammation with the use of any of the antiviral drugs available, particularly if the regimen does not include pegIFN/Riba. Clearly, none of these drugs directly manages the hepatic steatosis, which is a highly significant predictor of treatment failure or relapse (25). Thus the discovery that management of hepatic steatosis with either RYGB or orally administered Brake™ offers promise of another major advance in the treatment of hepatitis C infection.

By way of example and illustration of the role of an ileal brake compound or composition (Brake™) in hepatitis C treatment, the inventors describe here some patient cases to demonstrate unexpected favorable outcomes in difficult treatment cases with hepatitis C where the response was better than expected when the patient was given Brake™

| Aphoeline Formulation 1 |
| --- |
| 600 mg/capsule glucose |
| 1000 mg capsule |
| 10% Eudragit coating |
| Plasticizer (propylene glycol, triethyl acetate and water) |
| Magnesium stearate |
| Silicon Dioxide |

| Formulation II | | |
| --- | --- | --- |
| Blend: | Amount | Range |
| Alfalfa Leaf | 3.00 | 1-10+ |
| Chlorella Algae | 3.00 | 1-10+ |
| Chlorophyllin | 3.00 | 1-10+ |
| Barley Grass Juice Concentrate | 3.00 | 1-10+ |
| Dextrose | 1429.00 | 500-3000+ |
| Other Tablet Ingredients: | | |
| Coating* | 388.40 | 125-750+ |
| Corn Starch NF | 80.00 | 25-160+ |
| Hypromellose USP | 32.40 | 10-65+ |
| Stearic Acid NF (Vegetable Grade) | 19.50 | 6.5-35+ |
| Triacetin FCC/USP | 19.30 | 6.5-40+ |
| Magnesium Stearate NF/FCC | 7.00 | 2.5-15+ |
| Silicon Dioxide FCC | 2.50 | 0.75-5.0+ |

*Depending upon the composition used, 10% by weight Aqueous Shellac (Mantrose Haeuser, Inc. Aphoeline-1), 8% by weight Aqueous Indian Shellac (Aphoeline-2) was used to coat the formulations.

Formulation II was provided by mixing the actives with corn starch, stearic acid, magnesium stearate and silicon dioxide and pressing into a tablet, and coating the tablet with shellac (either 10% or 8% shellac), triacetin and the hypromellose. A Eudragit coating could alternatively be used, similar to that which coats formulation I, as described above.

Example 1. Comparison of the Impact of Brake™ in 18 Patients vs. RYGB in 15 Patients from the Perspective of Insulin Resistance, on Hepatic Enzymes and Triglycerides A. Brake™ Treatment Population Briefly, Aphoeline Brake™ formulation 2 (described above) was given for a minimum of 6 months to a group of 18 patients. Demographics of the 18 patients were as follows.

9 males, 9 females, ages 26-71
1 African, 1 Asian, 3 Hispanics, 13 Caucasians
11 pre/early diabetic with insulin resistance and elevated insulin, pro-insulin or HBA1c
9 patients with Fatty Liver, 2 with liver biopsies, 7 of these were diabetic or pre-diabetic
3 patients with Hepatitis C not on any antiviral treatments. Two of these had biopsy proven cirrhosis
All patients were given 10 gm Brake™ once Daily, orally, 4 hrs prior to their main meal
Patients treated and followed for 6 months
Serial laboratory and biomarkers including BMI, body weight, hepatic profiles, Triglycerides and lipid profiles, HBA1c measurements.

B. RYGB Reference Population

Reference population was 15 RYGB patients followed for 6 months. RYGB patients used as controls in this have been published (26) and the entire description of these cases is herein incorporated by reference. Briefly, 15 adults with morbid obesity and T2DM undergoing RYGB were studied. After an overnight fast, a baseline blood sample was collected the morning of surgery and at 180 days to assess changes in glycemia, insulin resistance, LPS, mononuclear cell nuclear factor (NF)-kappaB binding and mRNA expression of CD14, TLR-2, TLR-4, and markers of inflammatory stress. At 6 mo after RYGB, subjects had a significant decrease in body mass index (52.1+/−13.0 to 40.4+/−11.1), plasma glucose (148+/−8 to 101+/−4 mg/dL), insulin (18.5+/−2.2 mmuU/mL to 8.6+/−1.0 mmuU/mL) and HOMA-IR (7.1+/−1.1 to 2.1+/−0.3). Plasma LPS significantly reduced by 20+/−5% (0.567+/−0.033 U/mL to 0.443+/−0.022E U/mL). NF-kappaB DNA binding decreased significantly by 21+/−8%, whereas TLR-4, TLR-2, and CD-14 expression decreased significantly by 25+/−9%, 42+/−8%, and 27+/−10%, respectively. Inflammatory mediators CRP, MMP-9, and MCP-1 decreased significantly by 47+/−7% (10.7+/−1.6 mg/L to 5.8+/−1.0 mg/L), 15+/−6% (492+/−42 ng/mL to 356+/−26 ng/mL) and 11+/−4% (522+/−35 ng/mL to 466+/−35 ng/mL), respectively. We found that LPS, NF-kappaB DNA binding, TLR-4, TLR-2, and CD14 expression, CRP, MMP-9, and MCP-1 all decreased significantly after RYGB. The mechanism underlying resolution of insulin resistance and T2DM after RYGB may be attributable, at least in part, to the reduction of endotoxemia and associated inflammation, as shown by declines in pro-inflammatory mediators following RYGB. From a mechanistic perspective, the actions of RYGB and Brake™ on steatosis are summarized below:

L cell signaling is the primary function of RYGB and Brake™

Hepatic storage and release responses to Lipid exposure is controlled by the Gastrointestinal tract expression of L-cell hormones Excess Hepatic Lipid accumulation is secondary to altered or defective signaling resulting in an insult from a greater than needed supply of glucose and triglycerides, plus higher insulin exposure in an unbalanced response to the absorption of glucose Maintenance of Liver cells and control of insulin resistance is a primary benefit of controller L cells in the ileum. The action is that of the ileal brake.

Liver inflammatory response to virus and dietary carbohydrates and lipids is an end disorder of signaling maintenance and stimuli in the L cell pathways, and the inflammatory response to the virus Hepatitis C virus is easier controlled if the liver is optimally managed by L cell hormones and there is central control of the nutrients absorbed The comparative potency of Brake™ vs. the RYGB procedure is shown in Table 1 below. Brake™ was nearly as efficient at lowering insulin resistance and triglycerides and produced a greater overall lowering of hepatic enzymes than seen in the RYGB patients. There were no significant side effects, all Brake™ treated patients had beneficial weight loss, and overall there was a similar improvement in the health of the liver in both patient groups.

TABLE 1

Relative Potency: Brake vs. RYGB

| Parameter | N | Brake Mean | SD | N | RYGB Mean | SD | P Value | Brake as % of RYGB Change |
|---|---|---|---|---|---|---|---|---|
| % Weight loss, total in 6 mo | 18 | 5.29 | 4.01 | 15 | 25.23 | 5.88 | 0.203 | 20.97 |
| % Weight loss as excess kg in 6 mo | 18 | 5.4 | 48 | 15 | 44.9 | 14.4 | 0.006 | 12.03 |
| % chg HOMA-IR: pre to post change in 6 mo | 18 | 38.3 | 17.8 | 15 | 60.8 | 18.6 | 0.002 | 62.99 |
| % change HBA1c: pre to post change in 6 mo | 6 | 11.2 | 4.35 | 15 | 20.5 | 12.2 | 0.019 | 54.63 |
| % change AST: pre to post change in 6 mo | 15 | 41.3 | 21.7 | 15 | 26 | 22.9 | 0.071 | 158.0 |
| % change ALT: pre to post change in 6 mo | 16 | 50.5 | 20.5 | 13 | 26.9 | 31.0 | 0.028 | 187.0 |
| % change Triglycerides: pre to post change in 6 mo | 11 | 32.5 | 15.2 | 6 | 40.3 | 24 | 0.498 | 81.0 |

Only the patients who start out with abnormal baseline values are included in some calculations From this comparison study, it is postulated that RYGB and Brake™ might have a dual role in remediation of hepatic steatosis. Initially, the decline in insulin resistance, and lowered supply of triglycerides and glucose reduce fatty liver. Longer term, the decline in liver enzymes such as ALT, AST, GGTP and others as well as the decline in Alpha fetoprotein inform a Brake™ controlled anti-inflammatory pathway. In summary, the action of Brake™ on the liver is to reduce steatosis and reduce inflammation. Both mechanisms are applicable to Brake™ in combination improving the outcome of Hepatitis C antiviral therapy with these synergistic added benefits over the actions of the antiviral alone.

Example 2. Case 1: A Hepatitis C Patient with Moderate Viral Load Treated with Brake™ Alone, with the Goal to Evaluate the Secondary Antiviral Impact of Improving the Hepatic Steatosis Patient M1 was a 55 yo female with a normal BMI. She had a renal transplant in 1998 and has been taking prednisone, Rapimmune, Synthroid, Nexium and Cozaar.

Hepatitis C Genotype 3 in 1998, Failed Treatment IFN/Riba ~4 yr prior to this episode of care. Liver Biopsy 2004: Cirrhosis w. bridging fibrosis, stage 3/4

She was not on Hepatitis C treatment since 2007; no antiviral drugs in the 3 years prior to Brake™ therapy.

Figure 2:
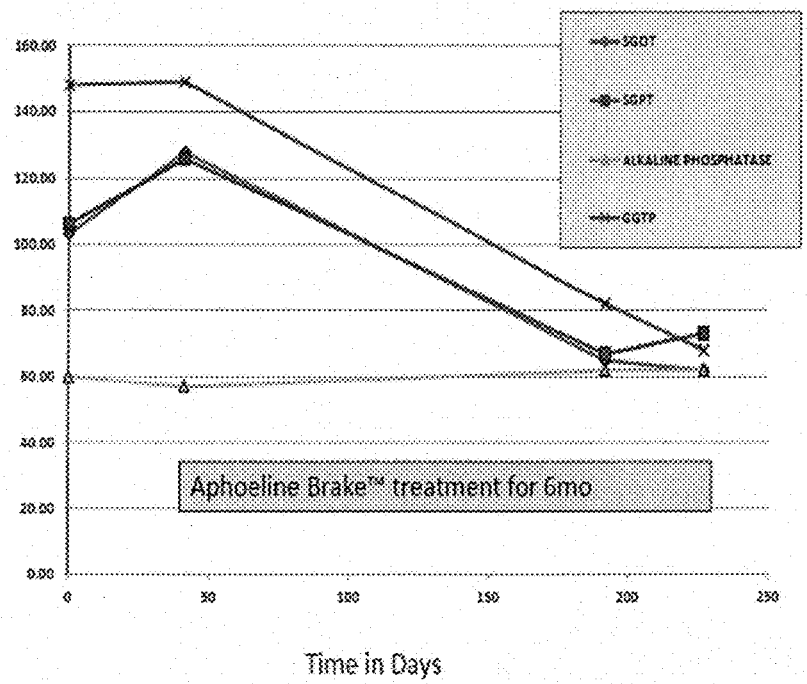
FIG. 2 shows the effect on hepatic parameters after administration of an ileal brake composition (formulation II) according to the present invention. Administration for six months shows a substantial impact on three of the four hepatic parameters followed.

Added Aphoeline Brake™ (formulation II) at second visit
Liver enzymes improved to normal over 3 mo
Creatinine decreased to normal over 3 mo
Alpha fetoprotein decreased rapidly
Hepatitis C Viral count decreased rapidly to 100K (See FIG. 1)
Patient M1 had one log reduction in viral titers
M1 had previously failed IFN/Riba in 2004, was immunosuppressed with prednisone and has established cirrhosis. It would have been a great surprise if this patient had viral eradication even for a short time.
Diabetes parameters were unaffected, (patient did not have T2D) Alpha fetoprotein declined from 8.5 ng/ml pre-treatment to <4 ng/ml post.
Hepatic enzymes all declined to normal on Brake™ therapy, even though the hepatitis C virus was still present in lower numbers.
Overall, there was an Unexpected but Interesting Improvement in Hepatic Function, without Major Changes in the Hepatitis C Viral Load (See FIG. 2)

Prior to these observations it was considered unlikely to improve hepatic steatosis unless the virus was eradicated. However, these results show that improving the hepatic steatosis actually improves the overall viral response, presumably by boosting the body's ability to respond to the viral effects with improved hepatic functioning.

Example 3. Case 2: A Hepatitis C Patient with Combination Treatment of Brake™ and pegIFN/Riba, a Test of the Ability of Combinations to Reduce Viral Load Over that of pegIFN/Riba Alone Patient E1 was a 36 year old male who was 5'7" 185 lb and had a BMI of 29 upon presentation for treatment of his hepatitis C genotype 1a TC virus. His pre-treatment liver biopsy showed hepatic steatosis and fibrosis 1 of 4. He was started on pegIFN/Riba with initial one log decline in viral load, but after the first month his dose was increased because of a plateau in viral load response. There was only a one log further decline. After two months with only moderate viral load response to this increased dosage, the patient had the addition of 10 gm per day of Aphoeline Brake™ added to his maximal dose pegIFN/Riba regimen.

Figure 3:
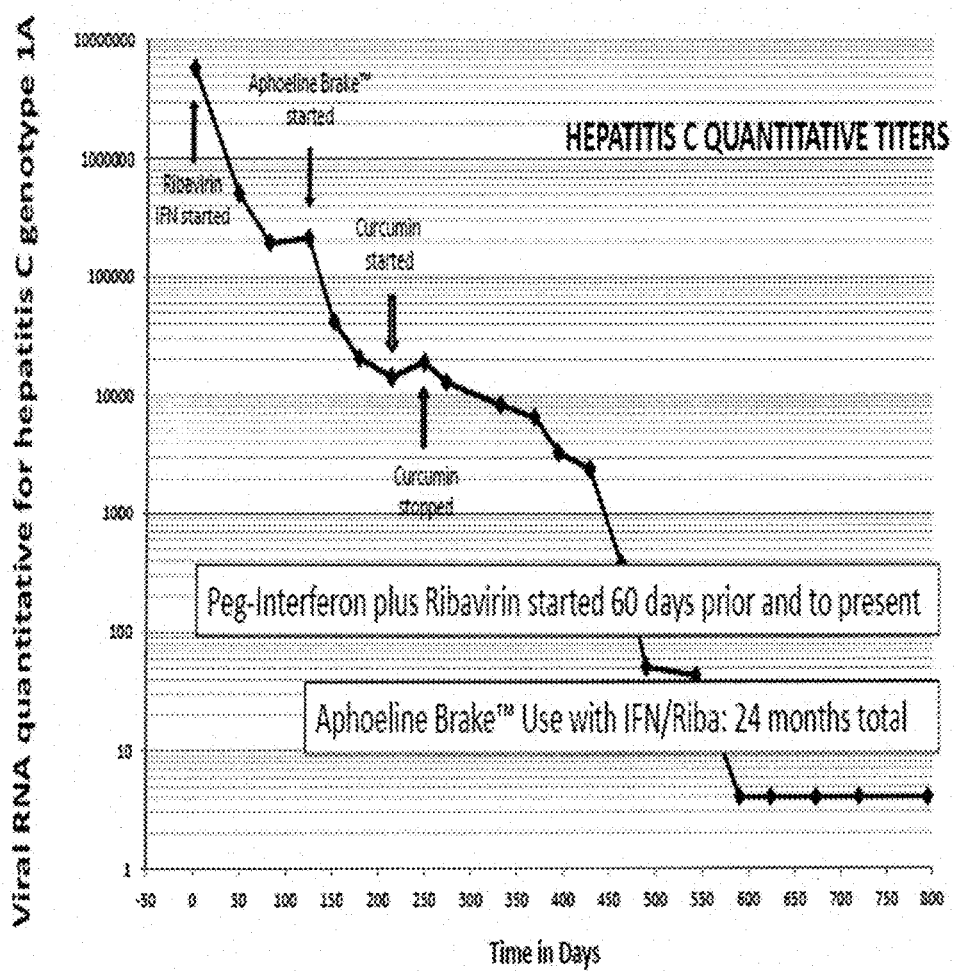
FIG. 3 shows the effect of Aphoeline II (Formulation II) added to treat Hepatitis C, Genotype 1a TC, treated with Riba/PegIFN. The figure shows a substantial reducing in viral titer with a formulation according to the present invention in combination with a standard therapeutic regimen of pegylated interferon and ribavirin.

As shown in FIG. 3 describing his viral load over time, he received this combination for 24 months and became negative for Hepatitis C virus for the past 10 months, which in the case is a 7 log decline in viral load. Thus, the viral load response to the ileal brake compound of formulation II plus the pegylated interferon and ribavirin is a synergistic result, because it far exceeds the antiviral actions of either compound alone or their expected additive effects. In the middle of his course of treatment, he started taking curcumin, with loss of control for viral load. This was not surprising as the action of Brake™ is antagonized by curcumin. After stopping curcumin his viral load again began to drop.

Figure 4:
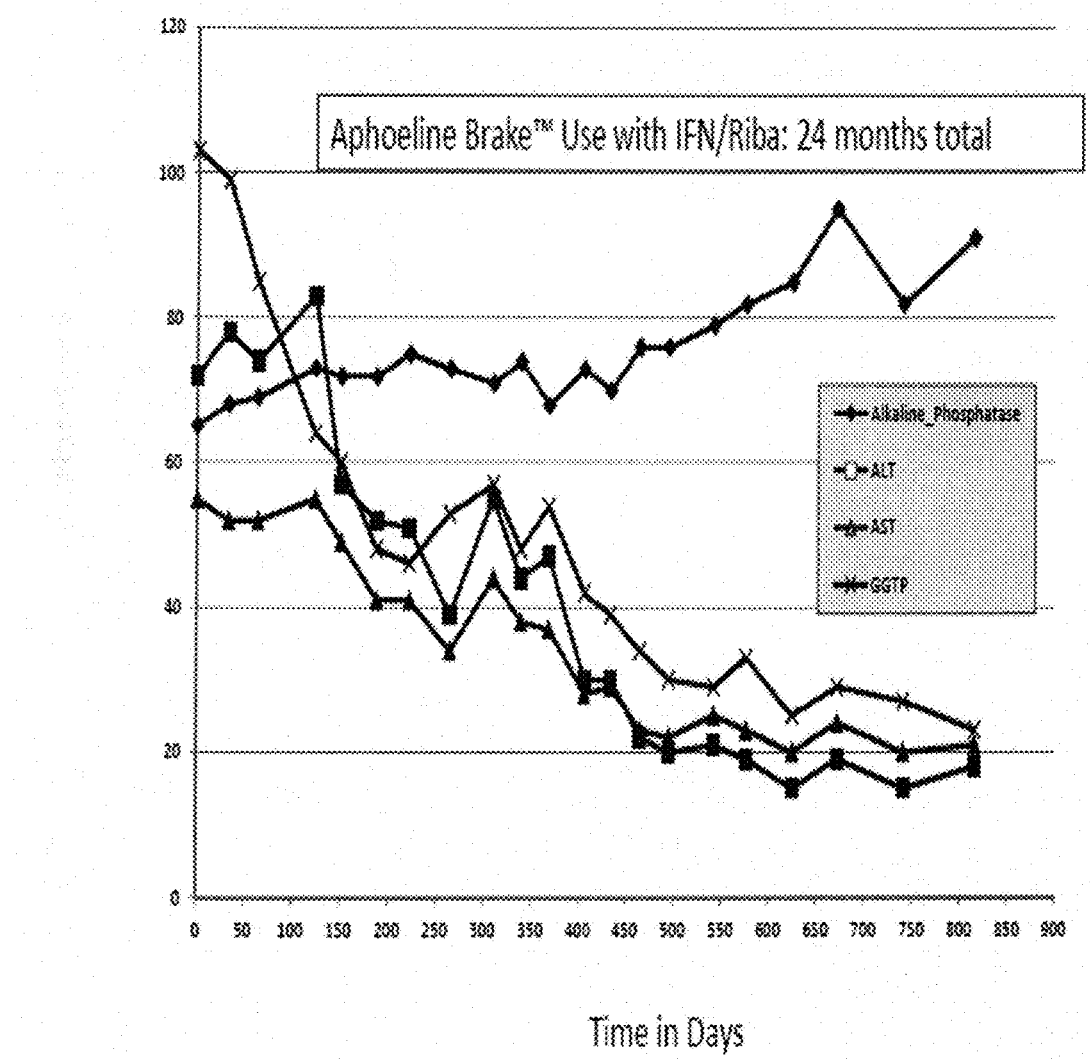
FIG. 4 shows the effect on hepatic parameters of a patient who was put on a combination of formulation II in combination with pegylated interferon and ribavirin for a period of 24 months.

On Formulation II, there has been major and unanticipated improvement of Liver health with regard to steatosis. The patient's initially elevated triglycerides and liver enzymes on pegylated interferon/ribavirin (see FIG. 4) which declined by less than 25% on the antiviral alone, are now normal, and there is no clinical evidence of steatosis at the present time. Thus, the 100% decline in hepatic inflammatory response to the combination of the brake compound (formulation II) and pegylated interferon/ribavirin was also synergistic in nature.

Figure 5:
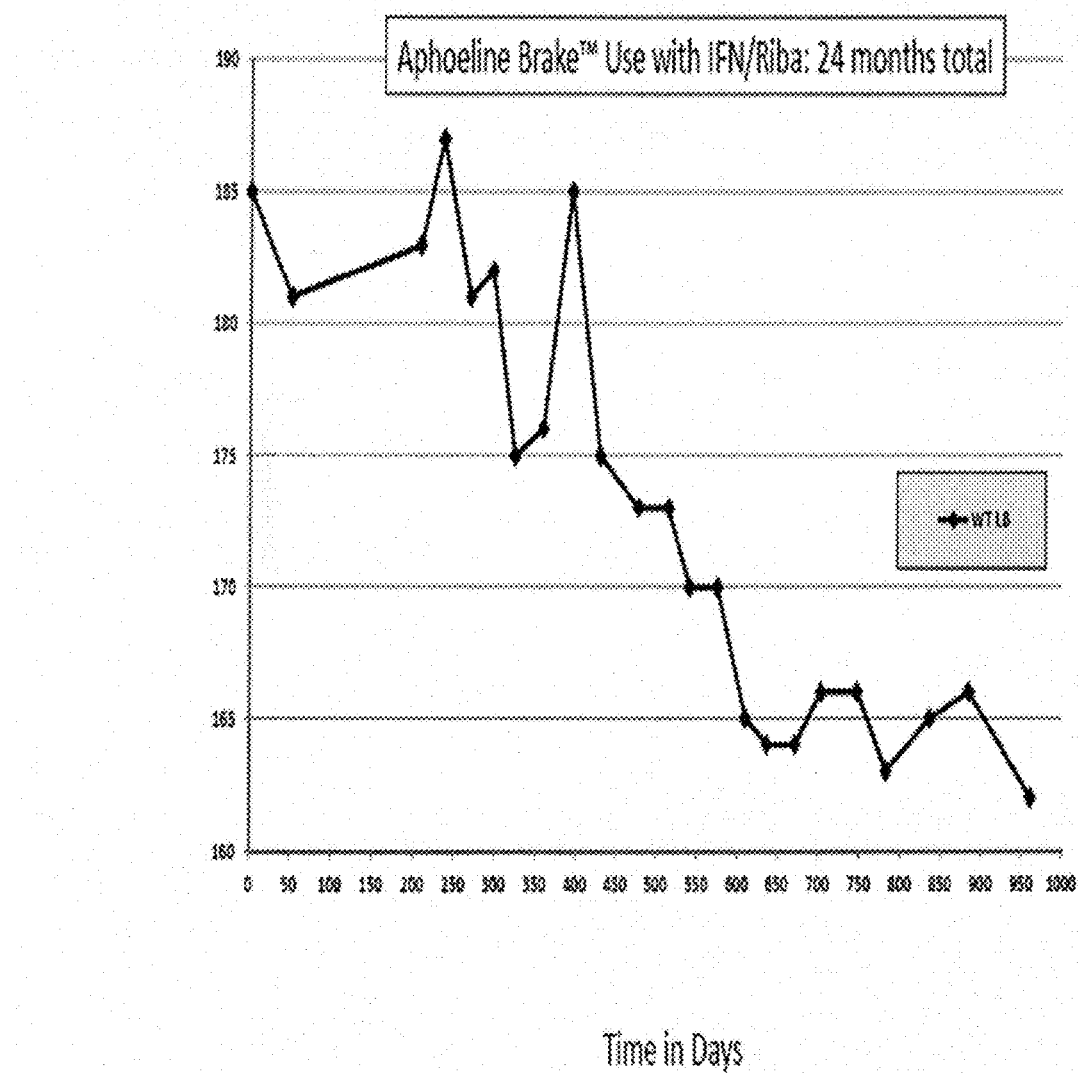
FIG. 5 shows effect on the weight of the patient from FIG. 4, above, after a period of 24 months. Note that the patient lost more than 20 pounds during that period.

Follow-up. After 24 months of treatment, the patient has lost 23 lb (see FIG. 5), continues to do well and is working. After beneficial (synergistic) response to the combination therapy for 24 months, antivirals and Brake™ are now stopped and the patient is in the 6-12 month follow-up phase to determine if the virus will return.

AFP is a glycoprotein of 591 amino acids and a carbohydrate moiety. Many functions have been proposed for AFP such as an anti-cancer active site peptide. Its function in adults is unknown, but a concentration above 500 ng/ml of AFP in adults can be indicative of hepatocellular carcinoma, germ cell tumors, and metastatic cancers of the liver. Alpha fetoprotein values above 10 ng/ml are considered a risk in hepatitis C patients, and the goal of therapy with pegIFN/Riba is to reduce the AFP below this value (27). Many patients with hepatitis C have elevated alpha fetoprotein concentrations. Alpha fetoprotein may be more closely linked to hepatic steatosis than to the hepatitis C viral load (28). Goldstein and colleagues (29) noted that patients with chronic viral hepatitis and cirrhosis often have elevated serum alpha-fetoprotein (AFP) values, and studied 81 patients with chronic hepatitis C. They examined the relationships of serum AFP and alanine aminotransferase (ALT) values, hepatic histologic features, and hepatocyte proliferation activity scores. Twenty-two of their patients had nil to mild fibrosis, 34 had moderate fibrosis, and 25 had marked fibrosis-cirrhosis. The mean serum AFP value was significantly greater in patients with more fibrosis. Serum ALT values were slightly greater in the marked fibrosis-cirrhosis patient group. Among all patients, increasing serum AFP values significantly correlated with increasing ALT values. There was no association between serum AFP values and immunohistochemical staining for AFP within hepatocytes. These results suggest that elevated serum AFP values are the result of altered hepatocyte-hepatocyte interaction and loss of normal architectural arrangements. The presence of marked fibrosis or cirrhosis, a state of significant altered hepatocyte architecture, may be the underlying cause of increased serum AFP, rather than necrosis or active regeneration. Others would agree with this view (27, 30-34), lending utility to use of declines in alpha-fetoprotein as a monitor of improving hepatic cellular architecture and decreasing risk for cirrhosis and possibly hepatocellular carcinoma.

Figure 6:
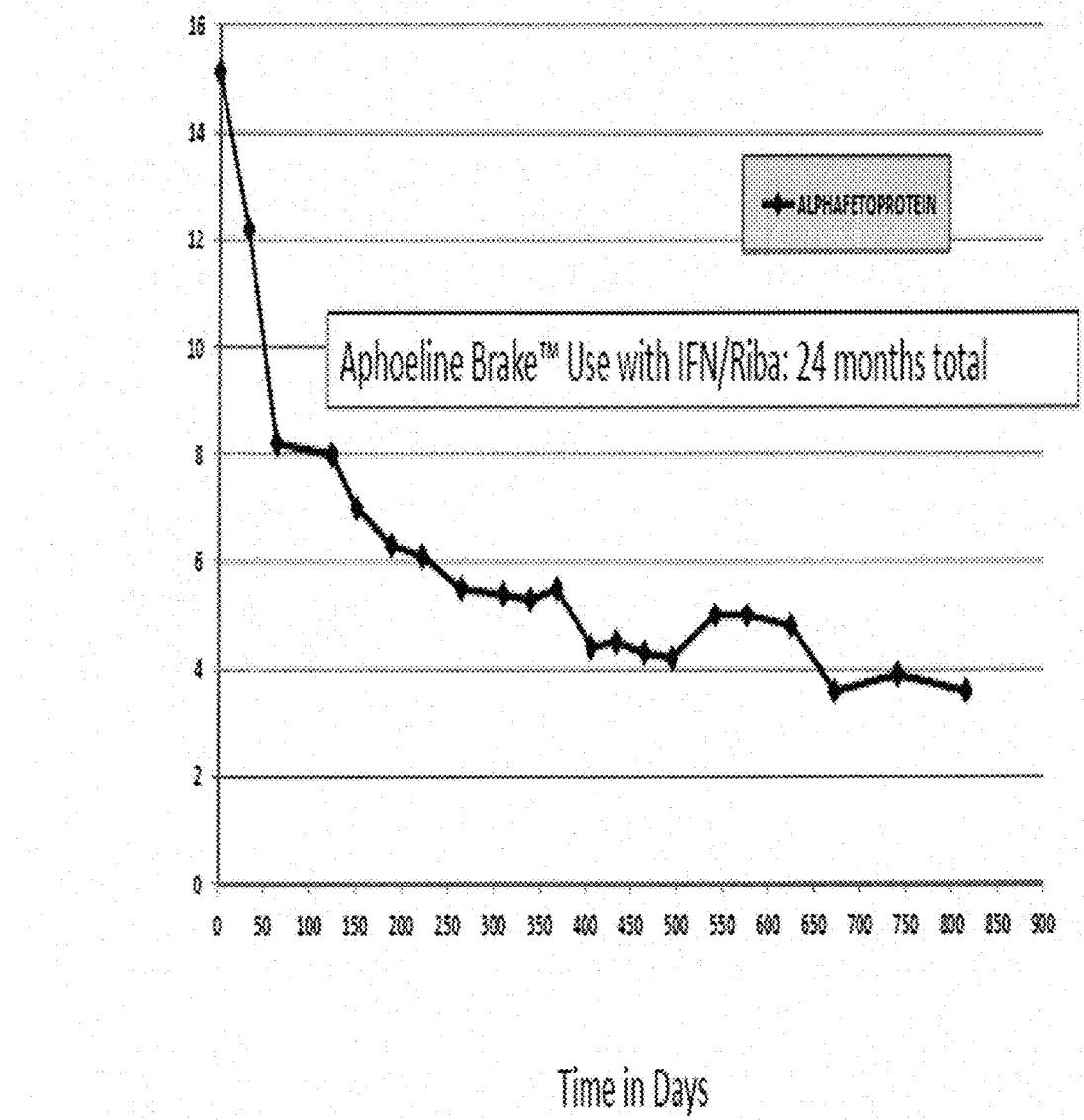
FIG. 6 shows effect of the ileal brake composition and viral combination therapy on alpha-fetoprotein after 24 months total therapy.

The graph of this biomarker for E1 over time is shown below as FIG. 6. From the pre-treatment AFP baseline of 15 ng/ml, there was an extensive decline in alpha fetoprotein in patient E1; this may indicate improvement in the health of the liver, a decline in steatosis, and a lower risk of cirrhosis under combined treatment with pegIFN/Riba and Brake™. Patient E1 had undetectable viral load in association with alpha fetoprotein values <4 ng/ml.

Figure 7:
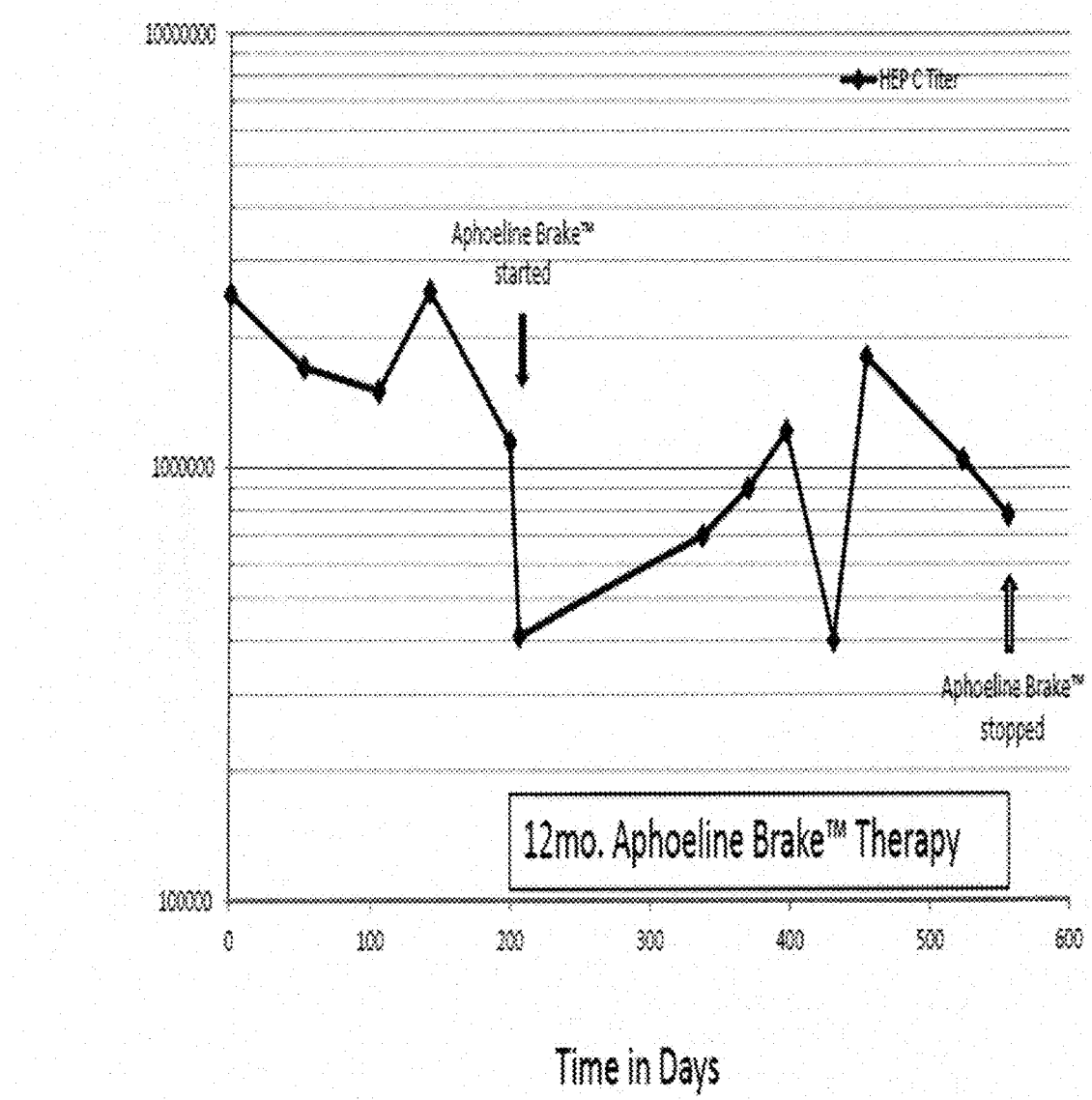
FIG. 7 shows the effect on Hepatitis C titers in a patient after 12 months of therapy on the ileal brake composition (formulation II).

Example 4. Case 3: A Hepatitis C Patient with Advanced Cirrhosis, Treated with Brake™ Alone, a Test of the Ability to Control Hepatic Steatosis in the Face of Minimal Action on the Viral Load Patient L1 is a 66 yo Overweight (5'3" 202 lb) but not overtly T2D female with Hepatitis C genotype 1a since ~2002. She had previously been treated with pegIFN/Riba but had been considered a failure in 2005. She has been untreated for Hepatitis C since that time. Her liver biopsy in 2006 revealed cirrhosis with fibrosis 4/4. Her bilirubin was 1.5 when seen and she was on the liver transplant list. Her chronic medications included spironolactone, rifaximin, and nexium. In view of this history she was given a course of Aphoeline Brake™ in 2010-2011, with a promising decline in viral load (approximately 1 log). This is illustrated in FIG. 7.

Figure 8:
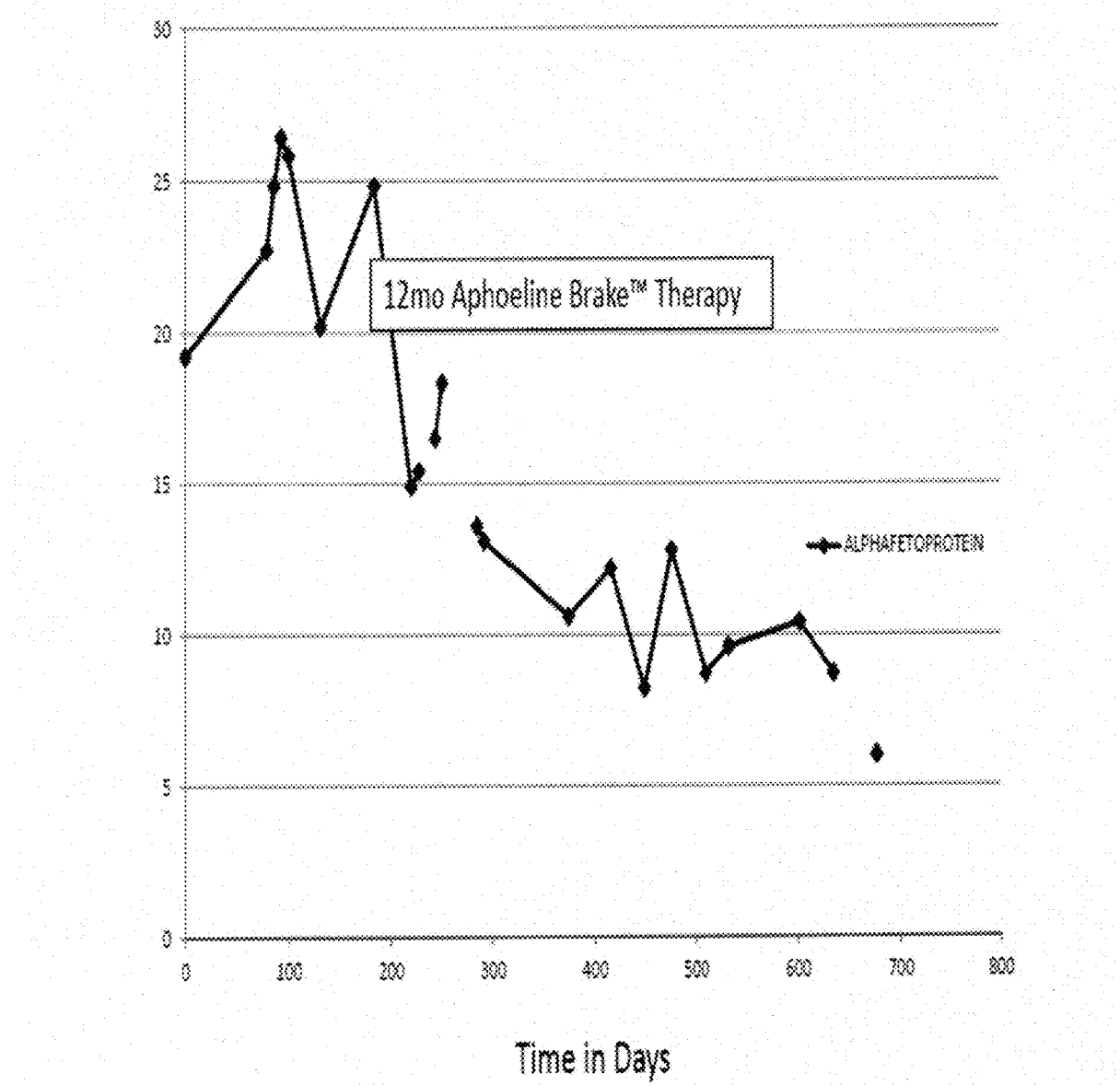
FIG. 8 shows the effect on alpha-fetoprotein on a patient (same patient as in FIG. 7) after 12 months of therapy on the ileal brake composition (formulation II).

The patient had markedly elevated alpha fetoprotein values, 25 ng/ml at baseline prior to treatment with Brake™. Values are illustrated in FIG. 8. During treatment over the next 12 months, these alpha fetoprotein values declined to 6 ng/ml, which is not normal but very good for a patient with 4/4 fibrosis and cirrhosis. This decline is related to the healing of the liver and the decline in steatosis, which may be entirely due to the administration of the ileal break composition (Aphoeline formulation II).

Figure 9:
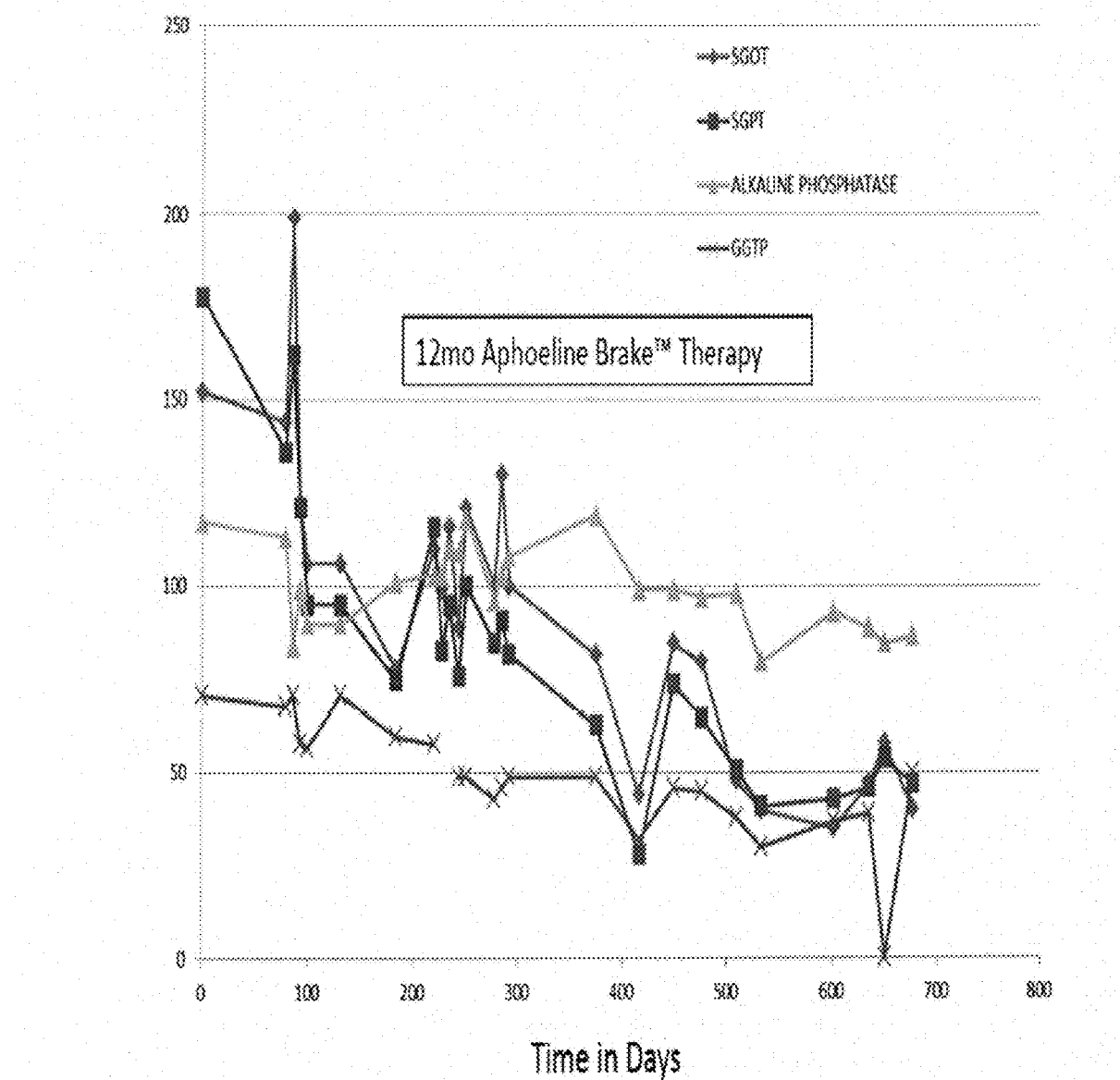
FIG. 9 shows that liver enzymes also decline, consistent with the healing, improvement in steatosis and the lowering of inflammation after 12 months of therapy on the ileal brake composition (formulation II).

Liver enzymes also decline, consistent with the healing, improvement in steatosis and the lowering of inflammation, as shown in FIG. 9. It was notable that her viral load was not reduced to negative, and in fact with 4/4 fibrosis it would not have been expected to see a negative viral load. However, the impact of Brake on the liver was clearly distinguishable in this case where there was only modest anti-viral associated effect itself. It therefore seems plausible to treat the hepatic steatosis, realizing that this will be of major benefit to the patient even without concomitant antiviral medication. The overall impression is that Brake is acting synergistically with endogenous antiviral activity, because the improving hepatic function itself can control the hepatitis C virus to some degree.

Followup: Brake™ clearly improved her hepatic function and this treatment alone was associated with decline in viral load. It is not expected that this decline in viral load was an anti-viral effect of Brake™, but rather it followed a marked improvement in her hepatic steatosis. Indeed although she was not subjected to a repeat of her biopsy, she clearly improved hepatic function by all measures. Bilirubin declined to 0.9 which is normal, she had no further episodes of encephalopathy and she returned to work as Lawyer. Total weight loss was 35 lb, and her weight stabilized at 170 lb. She was taken off the transplant list and was lost to FU in 2012.

Example 5. Disclosure of a Formulation of Brake™ that would be Effective in the Treatment of Hepatic Steatosis, in Patients with Hepatitis C that are Treated with Antiviral Agents The significant difference between normal and overweight or obese patients, is the response of the ileal brake to the intake of the mixed meal (35, 36), and more specifically to sugars. Therefore it seems the natural appetite suppressive pathways become tolerant to the intake of sugars. This partially explains the success of no carbohydrate programs such as the Adkins diet, even though in this case there are no demonstrable differences in the anatomy or histology of those two groups, except in rare cases of severe morbid long term obesity associated with atrophy of the ileum. Given the fact that food delivered to the distal intestine via RYGB is capable of stimulating those hormones independently of oral intake and the fact that the ileal stimulation during a mixed meal can be inhibited by suppressing the neurotransmission, it may be about the transmission of the signal from gut to brain. Ileal infusions of oleic acid in different amounts induced a dose-dependent increase of PYY (P<0.01) and a borderline decrease of motilin (P=0.05) levels (37), and these have central actions in appetite suppression. This study showed among its findings that the ileal brake effect on gastric emptying can be evoked by low doses of lipids in the distal ileum and that the delay of gastric emptying is related to the release of PYY. Both phenomena are dose dependent with regard to infused oleic acid. Thus the ileal brake is activated by lipids and sugars, and the optimal mixture can regulate a variety of the hormonal and immune-modulatory effects collectively considered that of the ileal brake itself.

It is probable from the oral Brake™ formulation work described herein, and that of the RYGB and supply side modeling of diabetes (26, 38, 39), that a reset of a carbohydrate-tolerant ileal brake pathway will re-set the control of the appetite center and down-regulate the feedback loop that interrupts eating (40), and the consequences of this down regulation of the ileal brake is acceleration of the dietary supply driven progression to a metabolic syndrome. Brake acts directly to restore this down-regulated appetite controller in those with obesity and T2D, the action is termed "wake up the Brake™".

With the promise of a beneficial interruption of hyperglycemia and hyper-triglyceridemia from decreased sugar and lipid intake (41, 42) indeed it appears that the supply side acting Brake™ (38, 39) is a primary means of controlling metabolic syndrome and the hepatic manifestation thereof, which is steatosis. Therefore if we are able to directly stimulate the ileum in the manner of RYGB with an orally administered formulation of Brake™, we should be able to restore the ileal brake signal and at least partially restore the visceral signals that control the intake of selected foods such as sugars and lipids. These control pathways also benefit hepatic steatosis treatment, since lipids accumulate in the liver itself.

These visceral signals are not only important to control of metabolic syndrome abnormalities but as reported in review articles (43-48) these hormones are extremely beneficial to the patient. They control the most fundamental of processes, which may be called eating behavior, and they do not extinguish or even reset with food deprivation diets (49). Their persistence during starvation diets could be what the patients are seeking unconsciously when they overeat in times of food in plenty.

The surprise of these hormonal ileal brake pathways is that they are down-regulated as patients overeat, allowing a new set point at a higher body weight and eventually leading to obesity and diabetes (50). Since these hormones are also very important in the homeostasis of the insulin and glucose levels they will help tremendously in the use of the reserves that are already present. Finally there is new evidence that gut derived inflammation of the liver and pancreas, itself an effect of food and intestinal bacteria, is regulated by the hormones released by the ileal brake pathway, and that for the first time RYGB surgery and oral administration of Brake™ control these long term inflammation pathways (26).

Figure 10:
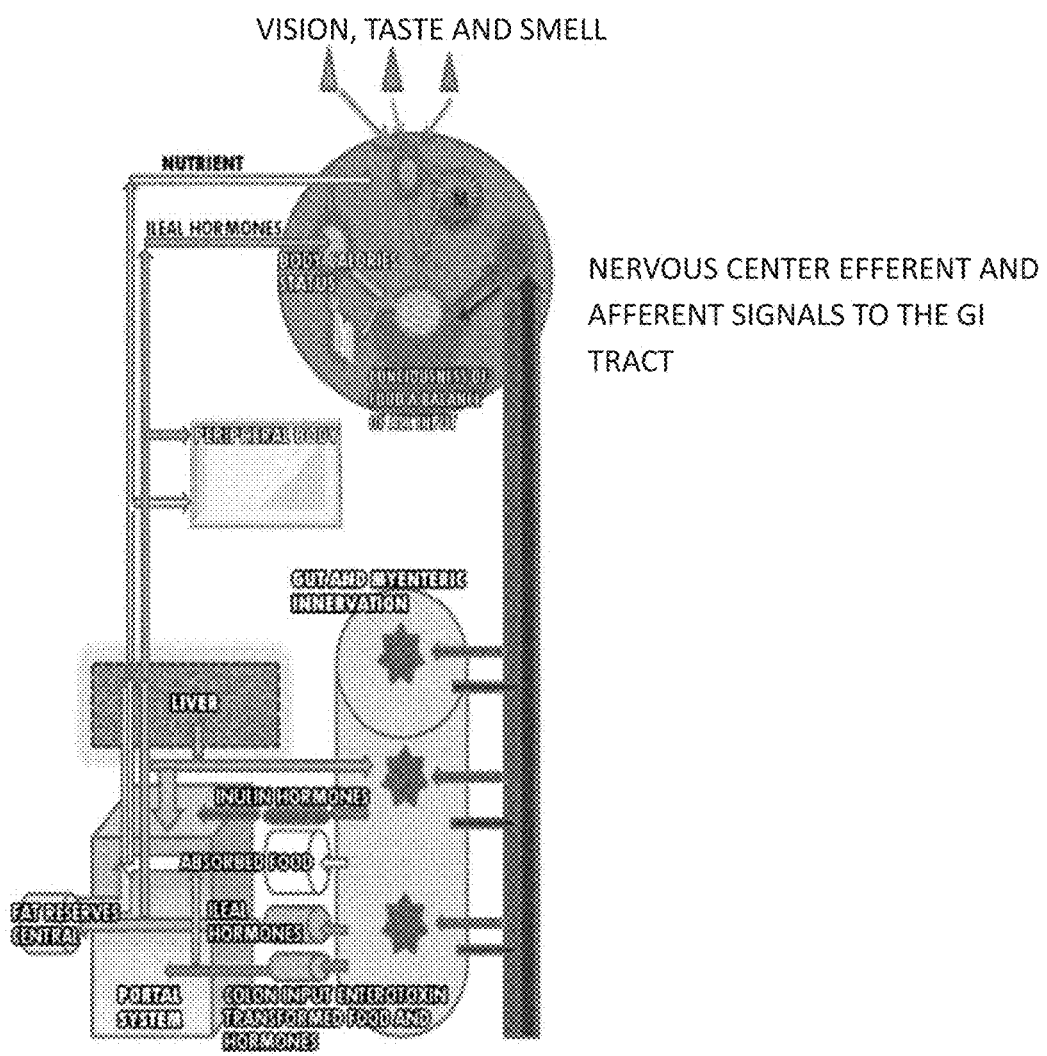
FIG. 10 shows a diagrammatic representation of a summary of the ileal brake pathways, which clearly places the portal system and the liver at the center of the regulatory organs in the diet and obesity axis. When the ileal brake pathway is out of control and over-eating accelerates, these controlling hormonal pathways lead to metabolic syndrome manifestations such as obesity, fatty liver disease, and atherosclerosis. Fatty liver disease is a precursor of fibrosis, cirrhosis and even hepatocellular carcinoma.

A summary of these pathways is provided as FIG. 10, which clearly places the portal system and the liver at the center of the regulatory organs in the diet and obesity axis.

When the ileal brake pathway is out of control and overeating accelerates, these controlling hormonal pathways lead to metabolic syndrome manifestations such as obesity, fatty liver disease, and atherosclerosis. Fatty liver disease is a precursor of fibrosis, cirrhosis and even hepatocellular carcinoma (51). Thus the use of Brake™ in patients with hepatic steatosis and hepatitis C is a novel means of controlling the underlying system that leads to progression of hepatocellular diseases in the presence of the hepatitis C virus, and the response of hepatic steatosis to RYGB surgery (52) predicts that oral use of Brake formulations would accomplish the same neuro-hormonal effects currently attributed to RYGB surgery.

By stimulating the endogenous and established hormones with Aphoeline Brake™ the present inventors are delivering the majority of the elucidated GI hormones where they belong (in the portal system), where they have the most powerful impact on the pancreas and the liver (53). We were also encouraged by the fact that RYGB surgery for obesity is capable of stimulating those hormones in essentially all patients, and the effects are apparent well before any weight loss occurs (52, 54-59), indicating that the patients with obesity, diabetes, and hepatic steatosis retain their innate ability to respond at the level of the ileal brake when normal hormonal levels are restored. Acting via these hormonal and neuro-hormonal pathways, RYGB changes the diets of patients, to lower their intake of refined sugars and fats, while shifting dietary preferences to intake of fruits and vegetables (60). Meat intake goes down and is more in moderation along with less fat, plant proteins and complex carbohydrates (60-68). Thomas and Marcus (69) further studied the issue of preference for fats by making a comparison of both food selection and food intolerance frequency of High-fat grouped foods versus Low-fat grouped foods in Roux-en-Y bariatric clients during their dietary adaptation phase (DAP). Thirty-eight bariatric surgery patients in their dietary transition phase (3 months-2.5 years) filled out a 236-food item questionnaire. From the larger set of primary data, 24 high-fat (30% or greater fat) and 22 low/lower-fat food items were itemized by selection frequency and food intolerance frequency for comparison. Briefly, high-fat food selection was 38.3% against low fat at 50.4% (p=0.0002). For comparison, the complete questionnaire's 236-item food selection percentage was 41%. Frequency of "Never" experiencing food intolerance was similar between both groups with a combined mean of 1.92%. "Seldom to Sometimes" intolerance in low-fat foods was 13.3%, and 24.9% in high fat (p=0.002). Finally, "Often to Always" experiencing food intolerance in the Low-fat food group was 85.5% versus 72.2% for the High-fat group (p=0.002). Overall, RYGB patients in the DAP demonstrated typical "dieting behavior" by selecting low-fat foods at a greater frequency than high-fat foods. Future bariatric studies are needed to further explore this and other commonly practiced "dieting behaviors" in bariatric patients. Leahey and colleagues (64) examined the effects of bariatric surgery on food cravings and especially sweet cravings, and also determined whether surgery patients' cravings differ from those of normal weight (NW) controls. Their objective was to examine changes in bariatric surgery patients' frequency of food cravings and consumption of craved foods from before to 3 and 6 months after surgery and to compare surgery patients' frequency of food cravings to those of NW controls. Bariatric surgery patients (n=32) and NW controls (n=20) completed the Food Cravings Inventory and had their height and weight measured. Before surgery, the patients reported more overall cravings and cravings for high fat and fast foods and a greater consumption of craved high-fat foods than the NW controls. Comparing overall findings from before to 3 and 6 months after surgery, the patients had significant reductions in overall cravings for, and consumption of, craved foods, with specific effects for sweets and fast food. Of interest, surgery had virtually no effect on the cravings for high-fat foods. Moreover, high-fat and fast food cravings did not reduce to normative levels. The postoperative patients were less likely to consume craved sweets than NW controls, and the patients' postoperative weight loss was largely unrelated to food cravings. Thus, Leahey found that bariatric surgery is associated with significant reductions in food cravings and consumption of craved foods, with the exception of high-fat foods. For these reasons the mixture of Brake™ invented for the improved management of hepatic steatosis and the dosages to be used are disclosed herein. Miras and colleagues (70) studied the pre and post-operative dietary habits and food preferences of patients who had bariatric surgery, and overall concluded that a fundamental aspect of the change caused by RYGB was in the taste for sweets and fats, and in most cases, taste favoring vegetables.

The inventors set a goal to stimulate the ileal hormones with an oral formulation of food component and generally recognized as safe (GRAS) ingredients, created to become an ileal brake hormone releasing substance that mimics the action of RYGB surgery. The data provided herein, derived from a comparison of Aphoeline Brake™ treated patients with RYGB are compelling and the stimulation of the ileal brake pathway seems independent of age or weight or diabetes (Table 1, above). This establishes that the intestine still functions in obesity, albeit with less hormonal oversight and control. Thus, the fundamental problem in both obesity and hepatic steatosis (fatty liver) seems to be in the down-regulation of the signaling from the ileum.

What we discovered from oral formulations targeted to the precise site which controls ileal brake hormone release, is that local stimulation of the ileum in this manner has a very powerful effect on the glucose and insulin homeostasis, leading to a rapid decline in of insulin resistance. Insulin resistance is the first major biomarker to change in response to either the oral use of Brake or to RYGB surgery. The inventors discovered that physiologically, the ileal brake pathway is not a means of further stimulating insulin, but in contrast to a prevailing viewpoint, a reduction of glucose supply-side delivery leads to a reduction of insulin resistance that occurs well before the patient begins to lose weight. This novel viewpoint is also consistent with the data from RYGB surgery, where the reduction in insulin resistance occurs within a few hours of surgical anastomosis, again much earlier than any weight loss.

The more powerful effect on steatohepatitis, observed in our patients by marked decline of the ALT, AST and GGTP to normal within 3-4 weeks of treatment with Aphoeline Brake™ need to be studied with before and after liver biopsy over a much longer duration of years, to confirm that the trend and the gains reported herein from laboratory data also apply to liver histology. However, it appears from the patient data and the RYGB data that the reduction in endotoxin, inflammation, insulin resistance and the trend to normalize triglyceride and cholesterol are all involved in rapid reduction of hepatic steatosis, just as occurs with bariatric surgery (52). The optimal formulation of Brake™ should consider the impact on hepatic lipid accumulation, itself under control of the mixture of signaling and mimetic substances reaching the ileal brake in RYGB. Various foods and components are beneficial beyond the glucose component and the lipid component, and some of these are incorporated by reference to the studies linking them to metabolic syndromes in model systems or epidemiological studies. For example, (71) Tulipani and colleagues examined changes in the urinary metabolome of subjects with metabolic syndrome, following 12 weeks of mixed nuts consumption (30 g/day), compared to sex- and age-matched individuals given a control diet. The urinary metabolome corresponding to the nut-enriched diet clearly clustered in a distinct group, and the multivariate data analysis discriminated relevant mass features in this separation. The metabolomics approach revealed 20 potential markers of nut intake, including fatty acid conjugated metabolites, phase II and microbial-derived phenolic metabolites, and serotonin metabolites. An increased excretion of serotonin metabolites was associated for the first time with nut consumption. Additionally, the detection of urinary markers of gut microbial and phase II metabolism of nut polyphenols confirmed the understanding of their bioavailability and bioactivity in the determination of the health effects derived from nut consumption. The results confirmed how a non-targeted metabolomics strategy may help to access unexplored metabolic pathways impacted by diet, thereby raising prospects for new intervention targets.

An ileal brake composition of micro-granules to control hepatic steatosis is informed by the research presented above and the results obtained from testing Aphoeline Brake™ in patients with hepatic steatosis, relies on the following analysis and information:

1. Hepatitis C is a chronic viral infection of 2% of the world's population that, if untreated, leads to progressive hepatic fibrosis and then cirrhosis.
2. A significant fraction of HCV infected patients develop hepatocellular carcinoma, but the usual cause of death is cirrhosis and its complications.
3. Hepatitis C is presently treated with the combination of pegylated interferon and ribavirin (pegIFN/Riba), but numerous agents have been synthesized and a number show promise as anti-HCV agents.
4. Two new antiviral agents have been introduced, these are telaprevir and boceprevir. Each of these two agents may be given alone or in combination with pegIFN/Riba in further combination with an ileal brake composition according to the present invention.
5. Changes in viral load result from these antiviral treatments alone, and if a patient can be converted to undetectable numbers of virus particles by such treatment, that is considered a favorable response to antiviral treatment.
6. If the patient with undetectable virus at the end of treatment does not relapse within 6-12 months, that patient might be considered cured of Hepatitis C by that treatment.
7. However, it is quite difficult to predict the course of Hepatitis C treatment from clinical parameters. However, when liver enzymes are elevated at the beginning of Hepatitis C therapy, and they rise further during treatment, that event usually defines increasing liver inflammation, treatment failure and would be expected to lead to progressive injury to the liver, thus exacerbating the disease state.
8. pegIFN/Riba responses are observed in slightly more than 50% of patients, and the response is correlated with a decline in numbers of viral particles, although not necessarily a cure. In treated patients with a decline in virus particles, liver enzymes such as ALT and AST may remain elevated but do not increase further, except on rare occasion as in the case of the advanced fibrosis and early on in the treatment, while in patients with no change in virus particles there is usually no associated decline in liver enzymes such as ALT and AST. It might be said that the decrease in the number of virus particles permits a decrease in hepatic inflammation, which then explains the decline in ALT and AST.
9. When the Hepatitis C virus particle count remains high and the liver enzymes are high or rising showing continued inflammation, then the unchecked Hepatitis C leads to cellular changes occurring in the liver which manifest as increasing fibrosis and eventually cirrhosis (a severe and irreversible form of hepatic fibrosis).
10. Hepatic Steatosis, or fatty liver disease, is commonly seen (25% of all adults over age 30). It is estimated that there are over 1.0 billion persons in the world with hepatic steatosis.
11. Hepatic Steatosis is associated with obesity, elevated serum triglycerides, type 2 diabetes, metabolic syndrome and diet high in fats or refined sugar.
12. Patients with hepatic steatosis usually have elevated liver enzymes.
13. There is no known effective treatment for hepatic steatosis except dietary decrease in sugars or fats and increased exercise/improved lifestyle/weight loss.
14. Depending on the study, the incidence of infection with hepatitis C in patients with Hepatic Steatosis is 3-6%, and more than 50% in association with genotype 3.
15. Patients with Hepatic steatosis who have infection with hepatitis C, are more difficult to treat with antivirals including pegIFN/Riba and resolution of the disease state is difficult.
16. When hepatic steatosis is present and hepatitis C is present in the same patient, treatment with antivirals alone often may not be associated with decline in the liver enzymes, because even elimination of the virus particles does not change the hepatic steatosis as the cause of elevation in the liver enzymes.
17. Thus the return of elevated liver enzymes to normal requires BOTH treatments to eradicate the hepatitis C virus AND treatment to resolve the hepatic steatosis. The surprising result is essentially a cure for hepatitis viral infections, something which can be obtained in only limited or rare instances using present protocol.
18. Treatments according to the present invention that work together to improve the disease and to eradicate an infection are synergistic in nature, because the combination is more effective than both components when provided alone, given an expectation for the additive benefits of combination therapy.
19. The presently claimed compounds, in particular, the ileal brake compounds and compositions according to the present invention are active against hepatic steatosis. These compounds alone may bring liver enzymes to normal in a patient with hepatic steatosis, including instances where the patient has a hepatitis viral infection (C or B, but most often C).
20. Of the hepatitis C drugs available, interferons may have the most capability for decreasing liver enzymes, more than the newer protease inhibitors at the same level of viral load decline. This may be explained by a general anti-inflammatory effect on the liver from interferons, and if this is true it justifies the use of other general liver treatments that are supportive of the liver in conjunction with antivirals. However, toxicity of the interferons, including liver toxicity, remains a potential problem.
21. The effect of the ileal brake compound/compositions alone on liver enzymes is greater than the effect of antiviral drugs for hepatitis C on liver enzymes.
22. The ileal brake compound/composition of the present invention alone is associated with only modest decline in the number of virus particles in a patient with hepatitis C. Usually, viral counts do not rise using an ileal brake compound alone and viral titers will fall, although they do not decline to low detection limits.
23. The experiments conducted and presented in the present application evidence that the ileal brake compound/composition according to the invention provides synergistic therapy in combination with antivirals for Hepatitis C, when the two are used in combination in patients who have hepatic steatosis secondary to viral infection.
24. Most patients (66+%) exhibit hepatic steatosis concomitant with hepatitis C infection.
25. When combined with any antiviral treatment for hepatitis C as described herein, the use of an ileal brake compound/composition will lower liver enzymes, resolve hepatic steatosis, reduce the likelihood and in certain instances, reverse cirrhosis of the liver and further help to lower virus particle counts in a patient with hepatitis C and hepatic steatosis as a secondary disease state and/or condition.

The teachings of the present invention further accommodate the following understandings and provide the following embodiments.

An ileal brake hormone releasing substance composition containing an effective amount of a sugar such as glucose, (including but not limited to dextrose and further including sucrose, and fructose, among other sugars) alone or in combination with oils (including but not limited to vegetable oils such as cottonseed, oils from most varieties of nuts, palm, corn, germ, olive, castor, sesame, fish oils including omega 3, oleic acid and derived liver oils) may be provided as an ileal brake composition. In the practice of the invention, when oils are used, they must be emulsified and allowed to become solids in emulsified form, and then coated for release in the ileum. When the ileal brake compositions of the present invention are produced to include both glucose and oil components as disclosed herein, the proportion of each of these components may vary from 10% by weight to 90% by weight. Indeed, in various aspects of the invention an ileal brake composition comprises a predominant glucose formulation (from about 50% to 90% by weight glucose or other sugar and about 10% to 50% of an oil as otherwise described herein), a predominant oil formulation (from about 50% to 90% by weight glucose or other sugar and about 10% to 50% of an oil as otherwise described herein) and about a 50:50 mixture (preferably a 50:50 by weight mixture) of glucoses and oils and remain entirely within the spirit of the invention, since optimal formulations and combinations thereof can be defined by the direct impact on biomarkers of the ileal brake and biomarkers of hepatic steatosis.

Other included ileal brake compositions as defined herein, optionally and preferably may comprise effective amounts of one or more of alfalfa leaf, chlorella algae, chlorophyllin and barley grass juice concentrate or sodium alginate, alone or in combination with the other ingredients or components.

The ileal brake compositions according to the present invention may be formulated with a delayed release base adapted to release the composition in the lower gut (ileum), that is, in a delayed and/or controlled release oral dosage form. The coated ingredients of the ileal brake composition of the present invention comprises micro granules or tablets have a pH dissolution profile that delays the release in vivo of the majority of the ileal brake hormone releasing substance (ileal brake compound) until the dosage form reaches the subject's ileum. A delayed and/or controlled release oral dosage form used in the invention can comprise a core containing an ileum hormonal-stimulating amount of an ileal brake hormone releasing substance that is coated by an enteric coating. Coatings for ileal brake compositions according to the present invention are selected from the group consisting of cellulose acetate trimellitiate (CAT), hydroxypropylmethyl cellulose phthalate (HPMCP), hydroxypropylmethyl cellulose, ethyl cellulose and mixtures of hydroxypropylmethyl cellulose and ethyl cellulose each of which contains a subcoating, polyvinyl acetate phthalate (PVAP), cellulose acetate phthalate (CAP), shellac, copolymers of methacrylic acid and ethyl acrylate, and copolymers of methacrylic acid and ethyl acrylate to which a monomer of methylacrylate has been added during polymerization. In some embodiments, the coating comprises Eudragit® L100 and shellac, or food glaze Eudragit® S100 in the range of 100 parts L100:0 parts S100 to 20 parts L100:80 parts S100, more preferably 70 parts L100:30 parts S100 to 80 parts L100:20 parts S100. As the pH at which the coating begins to dissolve increases, the thickness necessary to achieve ileum-specific delivery decreases. For formulations where the ratio of Eudragit® L100:S100 is high, a coat thickness of the order 150-200 μm can be used. For coatings where the ratio Eudragit® L100:S100 is low, a coat thickness of the order 80-120 μm can be used.

Oral dosage forms used in methods of preparation of ileal brake compositions according to the present invention can include one or more pharmaceutically acceptable carriers, additives, or excipients. The term "pharmaceutically acceptable" refers to a carrier, additive or excipient which is not unacceptably toxic to the subject to which it is administered. Pharmaceutically acceptable excipients are described at length by E. W. Martin, in "Remington's Pharmaceutical Sciences", among others well-known in the art. Pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

In addition to the preferred formulations of micro granules or tablets, exemplary dosage forms that will release the majority of the ileal brake hormone releasing substance in vivo upon reaching the ileum include oral dosage forms such as coated tablets, troches, lozenges, dispersible powders or granules, suspensions, emulsions or hard or soft capsules, each of which are formed after coating the ileal brake hormone releasing substance with an enteric coating. In the case of capsules, tablets and pills, the pharmaceutical compositions may also comprise buffering agents to maintain local pH at values below those that would allow the coating to disintegrate or dissolve. Solid compositions of a similar type may also be employed as fillers in soft and hard-filled gelatin capsules using such excipients as lactose or milk glucoses, as well as high molecular weight polyethylene glycols and the like.

REFERENCES

1. Marcellin P. Hepatitis C: the clinical spectrum of the disease. J Hepatol. 1999; 31 Suppl 1:9-16.
2. Butt A A, Kanwal F. Boceprevir and telaprevir in the management of hepatitis C virus-infected patients. Clin Infect Dis. 2012; 54(1):96-104.
3. Armstrong M J, Houlihan D D, Bentham L, Shaw J C, Cramb R, Olliff S, et al. Presence and severity of non-alcoholic fatty liver disease in a large prospective primary care cohort. J Hepatol. 2012; 56(1):234-40.
4. Dowman J K, Armstrong M J, Tomlinson J W, Newsome P N. Current therapeutic strategies in non-alcoholic fatty liver disease. Diabetes Obes Metab. 2011; 13(8):692-702.
5. Lok A S, Everhart J E, Chung R T, Kim H Y, Everson G T, Hoefs J C, et al. Evolution of hepatic steatosis in patients with advanced hepatitis C: results from the hepatitis C antiviral long-term treatment against cirrhosis (HALT-C) trial. Hepatology. 2009; 49(6):1828-37.
6. Briceno J, Ciria R, Pleguezuelo M, de la Mata M, Muntane J, Naranjo A, et al. Impact of donor graft steatosis on overall outcome and viral recurrence after liver transplantation for hepatitis C virus cirrhosis. Liver Transpl. 2009; 15(1):37-48.
7. Testino G, Sumberaz A, Ancarani A O, Borro P, Ravetti G, Ansaldi F, et al. Influence of body mass index, cholesterol, triglycerides and steatosis on pegylated interferon alfa-2a and ribavirin treatment for recurrent hepatitis C in patients transplanted for HCV and alcoholic cirrhosis. Hepatogastroenterology. 2009; 56(90):501-3.
8. Pekow J R, Bhan A K, Zheng H, Chung R T. Hepatic steatosis is associated with increased frequency of hepatocellular carcinoma in patients with hepatitis C-related cirrhosis. Cancer. 2007; 109(12):2490-6.
9. Ghany M G, Kim H Y, Stoddard A, Wright E C, Seeff L B, Lok A S. Predicting clinical outcomes using baseline and follow-up laboratory data from the hepatitis C long-term treatment against cirrhosis trial. Hepatology. 2011; 54(5):1527-37.
10. Thompson A J, Patel K, Chuang W L, Lawitz E J, Rodriguez-Torres M, Rustgi V K, et al. Viral clearance is associated with improved insulin resistance in genotype 1 chronic hepatitis C but not genotype 2/3. Gut. 2012; 61(1):128-34.
11. Lee W Y, Kwon C H, Rhee E J, Park J B, Kim Y K, Woo S Y, et al. The effect of body mass index and fasting glucose on the relationship between blood pressure and incident diabetes mellitus: a 5-year follow-up study. Hypertens Res. 2011; 34(10):1093-7.
12. Sung K C, Kim S H. Interrelationship between fatty liver and insulin resistance in the development of type 2 diabetes. J Clin Endocrinol Metab. 2011; 96(4):1093-7.
13. Dixon J B, Bhathal P S, Hughes N R, O'Brien P E. Nonalcoholic fatty liver disease: Improvement in liver histological analysis with weight loss. Hepatology. 2004; 39(6):1647-54.
14. Hickman I J, Russell A J, Prins J B, Macdonald G A. Should patients with type 2 diabetes and raised liver enzymes be referred for further evaluation of liver disease? Diabetes Res Clin Pract. 2008; 80(1):e10-2.
15. Forlani G, Di Bonito P, Mannucci E, Capaldo B, Genovese S, Orrasch M, et al. Prevalence of elevated liver enzymes in Type 2 diabetes mellitus and its association with the metabolic syndrome. J Endocrinol Invest. 2008; 31(2):146-52.
16. Kirpich I A, Solovieva N V, Leikhter S N, Shidakova N A, Lebedeva O V, Sidorov P I, et al. Probiotics restore bowel flora and improve liver enzymes in human alcohol-induced liver injury: a pilot study. Alcohol. 2008; 42(8): 675-82.
17. Fontana R J, Bonkovsky H L, Naishadham D, Dienstag J L, Sterling R K, Lok A S, et al. Serum fibrosis marker levels decrease after successful antiviral treatment in chronic hepatitis C patients with advanced fibrosis. Clin Gastroenterol Hepatol. 2009; 7(2):219-26.
18. Kwo P Y, Lawitz E J, McCone J, Schiff E R, Vierling J M, Pound D, et al. Efficacy of boceprevir, an NS3 protease inhibitor, in combination with peginterferon alfa-2b and ribavirin in treatment-naive patients with genotype 1 hepatitis C infection (SPRINT-1): an open-label, randomised, multicentre phase 2 trial. Lancet. 2010; 376 (9742):705-16.
19. Sherman K E, Flamm S L, Afdhal N H, Nelson D R, Sulkowski M S, Everson G T, et al. Response-guided telaprevir combination treatment for hepatitis C virus infection. N Engl J Med. 2011; 365(11):1014-24.
20. Bacon B R, Gordon S C, Lawitz E, Marcellin P, Vierling J M, Zeuzem S, et al. Boceprevir for previously treated chronic HCV genotype 1 infection. N Engl J Med. 2011; 364(13):1207-17.
21. Poordad F, McCone J, Jr., Bacon B R, Bruno S, Manns M P, Sulkowski M S, et al. Boceprevir for untreated chronic HCV genotype 1 infection. N Engl J Med. 2011; 364(13):1195-206.
22. Poordad F, Theodore D, Sullivan J, Grotzinger K. Medical resource utilisation and healthcare costs in patients with chronic hepatitis C viral infection and thrombocytopenia. J Med Econ. 2011; 14(2):194-206.
23. Poordad F. Big changes are coming in hepatitis C. Curr Gastroenterol Rep. 2011; 13(1):72-7.
24. Jacobson I M, McHutchison J G, Dusheiko G, Di Bisceglie A M, Reddy K R, Bzowej N H, et al. Telaprevir for previously untreated chronic hepatitis C virus infection. N Engl J Med. 2011; 364(25):2405-16.
25. Shah S R, Patel K, Marcellin P, Foster G R, Manns M, Kottilil S, et al. Steatosis is an independent predictor of relapse following rapid virologic response in patients with HCV genotype 3. Clin Gastroenterol Hepatol. 2011; 9(8): 688-93.
26. Monte S V, Caruana J A, Ghanim H, Sia C L, Korzeniewski K, Schentag J J, et al. Reduction in endotoxemia, oxidative and inflammatory stress, and insulin resistance after Roux-en-Y gastric bypass surgery in patients with morbid obesity and type 2 diabetes mellitus. Surgery. 2011.
27. Tamura Y, Yamagiwa S, Aoki Y, Kurita S, Suda T, Ohkoshi S, et al. Serum alpha-fetoprotein levels during and after interferon therapy and the development of hepatocellular carcinoma in patients with chronic hepatitis C. Dig Dis Sci. 2009; 54(11):2530-7.
28. Chen C H, Lin S T, Kuo C L, Nien C K. Clinical significance of elevated alpha-fetoprotein (AFP) in chronic hepatitis C without hepatocellular carcinoma. Hepatogastroenterology. 2008; 55(85):1423-7.
29. Goldstein N S, Blue D E, Hankin R, Hunter S, Bayati N, Silverman A L, et al. Serum alpha-fetoprotein levels in patients with chronic hepatitis C. Relationships with serum alanine aminotransferase values, histologic activity index, and hepatocyte MIB-1 scores. Am J Clin Pathol. 1999; 111(6):811-6.
30. Richardson P, Duan Z, Kramer J, Davila J A, Tyson G L, El-Serag H B. Determinants of Serum Alpha-Fetoprotein Levels in Hepatitis C Infected Patients. Clin Gastroenterol Hepatol. 2011.
31. Osaki Y, Ueda Y, Marusawa H, Nakajima J, Kimura T, Kita R, et al. Decrease in alpha-fetoprotein levels predicts reduced incidence of hepatocellular carcinoma in patients with hepatitis C virus infection receiving interferon therapy: a single center study. J Gastroenterol. 2011.
32. Tai W C, Hu T H, Wang J H, Hung C H, Lu S N, Changchien C S, et al. Clinical implications of alpha-fetoprotein in chronic hepatitis C. J Formos Med Assoc. 2009; 108(3):210-8.
33. Chen T M, Huang P T, Tsai M H, Lin L F, Liu C C, Ho K S, et al. Predictors of alpha-fetoprotein elevation in patients with chronic hepatitis C, but not hepatocellular carcinoma, and its normalization after pegylated interferon alfa 2a-ribavirin combination therapy. J Gastroenterol Hepatol. 2007; 22(5):669-75.
34. Di Bisceglie A M, Sterling R K, Chung R T, Everhart J E, Dienstag J L, Bonkovsky H L, et al. Serum alpha-fetoprotein levels in patients with advanced hepatitis C: results from the HALT-C Trial. J Hepatol. 2005; 43(3): 434-41.
35. Hoist J J. Glucagonlike peptide 1: a newly discovered gastrointestinal hormone. Gastroenterology. 1994; 107 (6):1848-55.
36. Ranganath L R, Beety J M, Morgan L M, Wright J W, Howland R, Marks V. Attenuated GLP-1 secretion in obesity: cause or consequence? Gut. 1996; 38(6):916-9.
37. Pironi L, Stanghellini V, Miglioli M, Corinaldesi R, De Giorgio R, Ruggeri E, et al. Fat-induced ileal brake in humans: a dose-dependent phenomenon correlated to the plasma levels of peptide Y Y. Gastroenterology. 1993; 105(3):733-9.
38. Monte S V, Schentag J J, Adelman M H, Paladino J A. Characterization of cardiovascular outcomes in a type 2 diabetes glucose supply and insulin demand model. J Diabetes Sci Technol. 2010; 4(2):382-90.
39. Monte S V, Schentag J J, Adelman M H, Paladino J A. Glucose supply and insulin demand dynamics of antidiabetic agents. J Diabetes Sci Technol. 2010; 4(2):365-81.
40. Guidone C, Manco M, Valera-Mora E, Iaconelli A, Gniuli D, Mari A, et al. Mechanisms of recovery from type 2 diabetes after malabsorptive bariatric surgery. Diabetes. 2006; 55(7):2025-31.
41. Welsh J B, Kannard B, Nogueira K, Kaufman F R, Shah R. Insights from a large observational database of continuous glucose monitoring adoption, insulin pump usage and glycemic control: the CareLink database. Pediatr Endocrinol Rev. 2010; 7 Suppl 3:413-6.
42. Welsh J A, Sharma A, Abramson J L, Vaccarino V, Gillespie C, Vos M B. Caloric sweetener consumption and dyslipidemia among US adults. Jama. 2010; 303(15): 1490-7.
43. Baynes K C, Dhillo W S, Bloom S R. Regulation of food intake by gastrointestinal hormones. Curr Opin Gastroenterol. 2006; 22(6):626-31.
44. Burcelin R, Da Costa A, Drucker D, Thorens B. Glucose competence of the hepatoportal vein sensor requires the presence of an activated glucagon-like peptide-1 receptor. Diabetes. 2001; 50(8):1720-8.
45. Drucker D J. Development of glucagon-like peptide-1-based pharmaceuticals as therapeutic agents for the treatment of diabetes. Curr Pharm Des. 2001; 7(14):1399-412.
46. Drucker D J. Glucagon-like peptide 2. J Clin Endocrinol Metab. 2001; 86(4):1759-64.
47. Boushey R P, Yusta B, Drucker D J. Glucagon-like peptide (GLP)-2 reduces chemotherapy-associated mortality and enhances cell survival in cells expressing a transfected GLP-2 receptor. Cancer Res. 2001; 61(2):687-93.
48. Drucker D J. Minireview: the glucagon-like peptides. Endocrinology. 2001; 142(2):521-7.
49. Sumithran P, Prendergast L A, Delbridge E, Purcell K, Shulkes A, Kriketos A, et al. Long-term persistence of hormonal adaptations to weight loss. N Engl J Med. 2011; 365(17):1597-604.
50. Maljaars P W, Peters H P, Mela D J, Masclee A A. Ileal brake: a sensible food target for appetite control. A review. Physiol Behav. 2008; 95(3):271-81.
51. El-Serag H B. Hepatocellular carcinoma. N Engl J Med. 2011; 365(12):1118-27.
52. Ochner C N, Gibson C, Shanik M, Goel V, Geliebter A. Changes in neurohormonal gut peptides following bariatric surgery. Int J Obes (Lond). 2011; 35(2):153-66.
53. Hvidberg A, Nielsen M T, Hilsted J, Orskov C, Holst J J. Effect of glucagon-like peptide-1 (proglucagon 78-107amide) on hepatic glucose production in healthy man. Metabolism. 1994; 43(1):104-8.
54. Reed M A, Pories W J, Chapman W, Pender J, Bowden R, Barakat H, et al. Roux-en-Y gastric bypass corrects hyperinsulinemia implications for the remission of type 2 diabetes. J Clin Endocrinol Metab. 2011; 96(8):2525-31.
55. Bikman B T, Zheng D, Pories W J, Chapman W, Pender J R, Bowden R C, et al. Mechanism for improved insulin sensitivity after gastric bypass surgery. J Clin Endocrinol Metab. 2008; 93(12):4656-63.
56. Morinigo R, Lacy A M, Casamitjana R, Delgado S, Gomis R, Vidal J. GLP-1 and changes in glucose tolerance following gastric bypass surgery in morbidly obese subjects. Obes Surg. 2006; 16(12):1594-601.
57. Morinigo R, Musri M, Vidal J, Casamitjana R, Delgado S, Lacy A M, et al. Intra-abdominal fat adiponectin receptors expression and cardiovascular metabolic risk factors in obesity and diabetes. Obes Surg. 2006; 16(6):745-51.
58. Morinigo R, Moize V, Musri M, Lacy A M, Navarro S, Marin J L, et al. Glucagon-like peptide-1, peptide Y Y, hunger, and satiety after gastric bypass surgery in morbidly obese subjects. J Clin Endocrinol Metab. 2006; 91(5):1735-40.
59. Plum L, Ahmed L, Febres G, Bessler M, Inabnet W, Kunreuther E, et al. Comparison of glucostatic parameters after hypocaloric diet or bariatric surgery and equivalent weight loss. Obesity (Silver Spring). 2011; 19(11):2149-57.
60. Olbers T, Bjorkman S, Lindroos A, Maleckas A, Lonn L, Sjostrom L, et al. Body composition, dietary intake, and energy expenditure after laparoscopic Roux-en-Y gastric bypass and laparoscopic vertical banded gastroplasty: a randomized clinical trial. Ann Surg. 2006; 244(5):715-22.
61. Ramon J M, Gonzalez C G, Dorcaratto D, Goday A, Benaiges A, Gonzalez S, et al. Quality of food intake after bariatric surgery: vertical gastrectomy versus gastric bypass. Cir Esp. 2011.
62. Overs S E, Freeman R A, Zarshenas N, Walton K L, Jorgensen J O. Food Tolerance and Gastrointestinal Quality of Life Following Three Bariatric Procedures: Adjustable Gastric Banding, Roux-en-Y Gastric Bypass, and Sleeve Gastrectomy. Obes Surg. 2011.
63. Shin A C, Berthoud H R. Food reward functions as affected by obesity and bariatric surgery. Int J Obes (Lond). 2011; 35 Suppl 3:S40-4.
64. Leahey T M, Bond D S, Raynor H, Roye D, Vithiananthan S, Ryder B A, et al. Effects of bariatric surgery on food cravings: do food cravings and the consumption of craved foods "normalize" after surgery? Surg Obes Relat Dis. 2012; 8(1):84-91.
65. Brunault P, Jacobi D, Leger J, Bourbao-Tournois C, Huten N, Camus V, et al. Observations regarding 'quality of life' and 'comfort with food' after bariatric surgery: comparison between laparoscopic adjustable gastric banding and sleeve gastrectomy. Obes Surg. 2011; 21(8):1225-31.
66. Shriner R L. Food as a bariatric drug. Curr Pharm Des. 2011; 17(12):1198-208.
67. Schweiger C, Weiss R, Keidar A. Effect of different bariatric operations on food tolerance and quality of eating. Obes Surg. 2010; 20(10):1393-9.
68. Suter M, Calmes J M, Paroz A, Giusti V. A new questionnaire for quick assessment of food tolerance after bariatric surgery. Obes Surg. 2007; 17(1):2-8.
69. Thomas J R, Marcus E. High and low fat food selection with reported frequency intolerance following Roux-en-Y gastric bypass. Obes Surg. 2008; 18(3):282-7.
70. Miras A D, le Roux C W. Bariatric surgery and taste: novel mechanisms of weight loss. Curr Opin Gastroenterol. 2010; 26(2):140-5.
71. Tulipani S, Llorach R, Jauregui O, Lopez-Uriarte P, Garcia-Aloy M, Bullo M, et al. Metabolomics unveils urinary changes in subjects with metabolic syndrome following 12-week nut consumption. J Proteome Res. 2011; 10(11):5047-58.

The invention claimed is:

1. A method of treating hepatic steatosis in a patient comprising orally administering an effective amount of an ileal brake composition in an oral dosage form comprising an ileal brake compound wherein at least 50% by weight of the ileal brake compound administered to said patient is released in the ileum of the patient.

2. The method according to claim 1 wherein the ileal brake composition lowers one or more of; elevated insulin resistance; elevated liver enzymes ALT and AST; and triglycerides.

3. The method according to claim 2 wherein the lowering one or more of; elevated insulin resistance; elevated liver enzymes ALT and AST; and triglycerides, mimics the effects of Roux-en-Y gastric bypass surgery (RYGB).

4. The method according to claim 1 wherein said patient is infected with hepatitis B or C and said ileal brake compound is coadministered with an antiviral agent.

5. The method according to claim 4 wherein said patient is infected with hepatitis C.

6. The method according to claim 4 wherein viral counts in said patient are effectively lowered, and the health of steatotic cells in the liver of said patient, are improved.

7. The method according to claim 4 wherein said antiviral agent is ribavirin, pegylated interferon, boceprevir, daclatasvir, asunapavir, INX-189, FV-100, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA- 034, MK-0608, A-837093, GS 9190, GS 9256, GS 9451, GS 5885, GS 6620, GS 9620, GS9669, ACH-1095, ACH-2928, GSK625433, TG4040 (MVA-HCV), A-831, F351, NS5A, NS4B, ANA598, A-689, GNI-104, IDX102, ADX184, ALS-2200, ALS-2158, BI 201335, BI 207127, BIT-225, BIT-8020, GL59728, GL60667, PSI-938, PSI-7977, PSI-7851, SCY-635, TLR9 Agonist, PHX1766, SP-30 or a mixture thereof.

8. The method according to claim 4, wherein the antiviral agent is an effective amount of pegylated interferon in combination with ribavirin.

9. The method according to claim 4, wherein the antiviral agent is pegylated interferon and/or ribavirin, further combined with boceprevir in a dosage of at least 800 mg three times daily.

10. The method according to claim 4, wherein the antiviral agent is pegylated interferon and/or ribavirin, further combined with telaprevir in a dosage of at least 750 mg three times daily.

11. The method according to claim 4, wherein the antiviral agent is an effective amount of daclatasvir, asunaprevir or a mixture thereof, optionally in further combination with an effective amount of pegylated interferon and/or ribavirin.

12. The method according to claim 4, wherein the antiviral agent is an effective amount of daclatasvir alone or in combination with an effective amount of pegylated interferon and/or ribavirin.

13. The method according to claim 4, wherein the antiviral agent is an effective amount of asunaprevir alone or in combination with an effective amount of pegylated interferon and/or ribavirin.

14. The method according to claim 4, wherein the antiviral agent is an effective amount of INX-189, alone or in combination with an effective amount of pegylated interferon and/or ribavirin.

15. The method according to claim 4, wherein the antiviral agent is an effective amount of FV-100 alone or in combination with an effective amount of pegylated interferon and/or ribavirin.

16. A method for producing an oral ileal brake compound composition which comprises the steps of:
 1) coating the ileal brake compound with a material which has a pH dissolution or time delayed profile that delays the release in vivo of the majority of the ileal brake compound until the dosage form reaches the subject's ileum; and
 2) coating the ileal brake compound inside a microparticle to form a population of microparticles, said microparticles releasing the compound at pH values specific to the coating within the range of about 7.0 to about 7.8.

17. The method according to claim 1 wherein a majority of the ileal brake compound is released from the dosage form when the dosage form reaches the patient's ileum, whereupon the ileal brake composition may either activate or re-activate the L-cells of the ileum and thereby produce all of the chemical and physiological characteristics of an activated ileal brake in a manner similar to RYGB surgery.

18. The method according to claim 17, wherein the ileal brake compound microparticles comprise a core which are coated by an enteric coating, wherein the coating thickness controls the dissolution of said ileal brake compound from said microparticles, thereby delaying release of the majority of the ileal brake compound until the microparticles reach the patient's ileum.

\* \* \* \* \*